United States Patent [19]

Selby

[11] Patent Number: 5,110,347

[45] Date of Patent: May 5, 1992

[54] SUBSTITUTED FUSED HETEROCYCLIC HERBICIDES

[75] Inventor: Thomas Selby, Wilmington, Del.

[73] Assignee: E. I Du Pont de Nemours and Company, Wilmington, Del.

[21] Appl. No.: 617,707

[22] Filed: Nov. 26, 1990

[51] Int. Cl.$^5$ .................. A01N 43/60; C07D 241/42; C07D 241/44; C07D 253/10
[52] U.S. Cl. .......................... 71/92; 71/93; 71/94; 544/183; 544/234; 544/235; 544/279; 544/283; 544/350; 544/353; 544/354; 544/356; 546/122; 546/157; 546/173; 556/87
[58] Field of Search ...................... 544/353, 354, 356; 71/92

[56] References Cited

U.S. PATENT DOCUMENTS 3,291,757  12/1966  Sturm et al. ................... 544/353
3,453,365   7/1969  Lane et al. .................... 544/353
3,900,473   8/1975  Diel et al. ..................... 544/356

OTHER PUBLICATIONS

Gogte et al., *Indian Journal of Chemistry*, 19B, pp. 1011–1013 (1980).
Selby, Chemical Abstracts, vol. 113, No. 191375 (1990) (Abstract for EP 353902).

Primary Examiner—Mukund J. Shah
Assistant Examiner—E. Bernhardt

[57] ABSTRACT

The invention relates to certain substituted fused compounds of Formula I

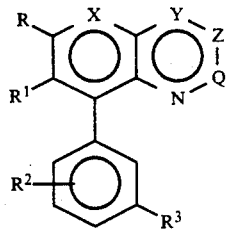

which are useful as herbicides, and their agriculturally suitable compositions, as well as methods for their use as general or selective preemergent or postemergent herbicides or as plant growth regulants.

21 Claims, No Drawings

SUBSTITUTED FUSED HETEROCYCLIC HERBICIDES

BACKGROUND OF THE INVENTION

This invention relates to certain substituted fused heterocyclic compounds which are useful as herbicides and their agriculturally suitable compositions as well as methods for their use as general or selective preemergent or postemergent herbicides or as plant growth regulants.

New compounds effective for controlling the growth of undesired vegetation are in constant demand. In the most common situation, such compounds are sought to selectively control the growth of weeds in useful crops such as cotton, rice, corn, wheat and soybeans, to name a few. Unchecked weed growth in such crops can cause significant losses, reducing profit to the farmer and increasing costs to the consumer. In other situations, herbicides are desired which will control all plant growth. Examples of areas in which complete control of all vegetation is desired are areas around railraod tracks, storage tanks and industrial storage areas. There are many products commercially available for these purposes, but the search continues for products which are more effective, less costly and environmentally safe.

EP-A-353,902 discloses herbicidal compounds of the formula

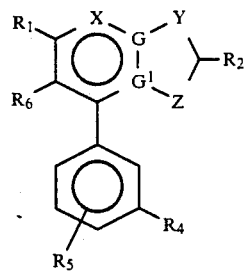

wherein, inter alia
G and $G^1$ are N and C; and
X, Y and Z are independently $CR_7$ or N.

Ind. J. Chem. 1980, 19B, 1011–1013 discloses without teaching herbicidal utility compounds of the formula

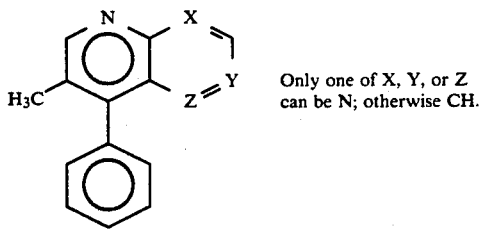

Only one of X, Y, or Z can be N; otherwise CH.

SUMMARY OF THE INVENTION

This invention comprises compounds of Formula I, agriculturally suitable compositions containing them, and their method-of-use as preemergence and/or postemergence herbicides or plant growth regulants.

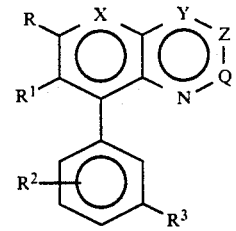

wherein
X is N or CH;
Y is N or $CR_8$;
Z is N, $CR^4$ or $CR^5$;
Q is N, $CR^4$ or $CR^5$;
R is $C_1$–$C_4$ alkyl, $C_2$–$C_4$ alkoxyalkyl, $C_2$–$C_4$ alkenyl, $C_2$–$C_4$ alkynyl, $C_1$–$C_4$ alkoxy, $C_1$–$C_4$ alkylthio, $C_1$–$C_3$ alkylamino or $N(C_1$–$C_3$ alkyl)($C_1$–$C_3$ alkyl);
$R^1$ is H, F, Cl or $CH_3$;
$R^2$ is H, halogen, $C_1$–$C_3$ alkyl, $C_1$–$C_3$ haloalkyl, $C_1$–$C_3$ alkoxy or $C_1$–$C_3$ haloalkoxy;
$R^3$ is H, halogen, $C_1$–$C_4$ alkyl, $C_2$–$C_4$ alkenyl, $C_2$–$C_4$ haloalkyl, $C_1$–$C_4$ haloalkyl, $C_3$–$C_4$ halocycloalkyl, $C_2$–$C_4$ haloalkenyl, $C_2$–$C_4$ haloalkynyl, $OR^6$, $S(O)_nR^7$ or CN;
$R^4$ is H, CN, $C_1$–$C_3$ alkyl, $C_1$–$C_3$ alkoxy or halogen;
$R^5$ is $C_1$–$C_4$ haloalkyl, $C_3$–$C_5$ halocycloalkyl, $C_2$–$C_4$ haloalkenyl, $C_2$–$C_4$ haloalkynyl, $OR^6$, $S(O)_nR^7$ or halogen;
$R^6$ is $C_1$–$C_4$ alkyl, $C_3$–$C_4$ alkenyl, $C_3$–$C_4$ alkynyl, $C_1$–$C_4$ haloalkyl, $C_2$–$C_4$ haloalkenyl or $C_2$–$C_4$ haloalkynyl;
$R^7$ is $C_1$–$C_2$ alkyl or $C_1$–$C_2$ haloalkyl;
$R^8$ is H, CN, $C_1$–$C_3$ alkyl, $C_1$–$C_3$ alkoxy or halogen; and
n is 0, 1 or 2.
and their mono N-oxides and their agriculturally suitable salts, provided that:
(a) when Z is N or $CR^4$, then Q is $CR^5$; and
(b) when Q is N or $CR^4$, then Z is $CR^5$.

In the above definitions, the term "alkyl", used either alone or in compound words such as "alkylthio" or "haloalkyl" includes straight chain or branched alkyl, e.g., methyl, ethyl, n-propyl, isopropyl or the different butyl isomers.

"Alkoxy", "alkenyl" and "alkynyl" analogously also includes straight chain or branched isomers.

"Halogen", either alone or in compound words such as "haloalkyl", means fluorine, chlorine, bromine or iodine. Further, when used in compound words such as "haloalkyl" said alkyl may be partially or fully substituted with halogen atoms, which may be the same or different. Examples include $CF_3$, $CH_2CF_3$, $CH_2CH_2F$, $CF_2CF_3$ and $CH_2CHFCl$.

Preferred for reasons including ease of synthesis and/or greater herbicidal efficacy are:
1. Compounds of Formula I wherein
   $R^1$ is H or F; and
   $R^2$ is H or F.
2. Compounds of Preferred 1 wherein
   $R^3$ is F, Cl, Br, $C_1$–$C_4$ haloalkyl, $OR^6$, $S(O)_nR^7$ or CN;
   n is 0;
   Y is N, CH or C—CN; and their mono N-oxides.
3. Compounds of Preferred 2 wherein
   R is $C_1$–$C_3$ alkyl, $C_2$–$C_3$ alkoxyalkyl, $C_2$–$C_3$ alkenyl, $C_2$–$C_3$ alkynyl, $C_1$–$C_2$ alkoxy, $C_1$–$C_2$ alkylthio, $C_1$-$C_2$ alkylamino and N($C_1$-$C_2$ alkyl)($C_1$-$C_2$ alkyl);

$R^6$ is $C_1$-$C_3$ alkyl, allyl, propargyl, $C_1$-$C_3$ haloalkyl, $C_2$-$C_3$ haloalkenyl.

4. Compounds of Preferred 3 wherein Z is N, CH or C—CN.

Specifically Preferred for reasons of greatest ease of synthesis and/or greatest herbicidal efficacy are:

2-(difluoromethoxy)-6-methyl-8-[3-(trifluoromethyl)-phenyl]quinoxaline;

7-methyl-3-(2,2,2-trifluoroethoxy)-5-[3-(trifluoromethyl)phenyl]-1,2,4-benzotriazine 1-oxide;

7-methyl-3-(2,2,2-trifluoroethoxy)-5-[3-(trifluoromethyl)phenyl]-1,2,4-benzotriazine; and 6-methyl-2-(trifluoromethyl)-8-[3-(trifluoromethyl)-phenyl]quinoxaline.

DETAILED DESCRIPTION OF THE INVENTION

Compounds of General Formula I can be readily prepared by one skilled in the art by using the reactions and techniques described in Schemes 1-10 and Equations 1-5 of of this section as well as by following the specific procedures given in Examples 1-7.

Scheme 1 illustrates the preparation of compounds of General Formula I (where R, $R^1$, $R^2$, $R^3$ X, Y, Z, and Q are defined as above) whereby heterocycles of Formula II where G is bromine or iodine can be coupled with substituted aryl compounds of Formula III where J is a trialkyltin (e.g. $Me_3Sn$), trialkylsilyl (e.g. $Me_3Si$), or a boronic acid (e.g. $B(OH)_2$) moiety. The coupling is carried out using methods known in the art: Tsuji, J., *Organic Synthesis* with *Palladium Compounds*, Springer-Verlag, Berlin, 1980; Negishi, E., *Acc. Chem. Res.* 1982, 15, 340; Stille, J. K., *Angew. Chem.* 1986, 98, 504; Yamamoto, A., Yamagi, A., *Chem. Pharm. Bull.* 1982, 30, 1731 and 2003; Dondoni, A., Fogagnolo, M., Medici, A., Negrini, E., *Synthesis* 1987, 185; Dondoni, A., Fantin, G., Fogagnolo, M., Medici A., Pedrini, P., *Synthesis* 1987, 693; Hoshino, Y., Miyaura, N., Suzuki, A., *Bull. Chem. Soc. Jpn.* 1988, 61, 3008; Sato, M., Miyaura, N., Suzuki, A., *Chem. Lett.* 1989, 1405; Miyaura, N., Yanagi, T., Suzuki, A. *Synthetic Commun.* 1981, 11, 513; Siddiqui, M. A., Snieckus, V., *Tetrahedron Lett.* 1988, 29, 5463; Sharp, M. J., Cheng, W., Snieckus, V., *Tetrahedron Lett.* 1987, 28, 5093; Hatanaka, Y., Fukushima, S., Hiyama,, T., *Chem. Lett.* 1989, 1711; Bailey, T. R., *Tetrahedron Lett.* 1986, 27, 4407. The coupling of II and III is carried out by heating in the presence of a transition metal catalyst such as tetrakis(triphenylphosphine)palladium(0) or bis(triphenylphoshine)palladium(II) dichloride in a polar or nonpolar aprotic solvent such as acetonitrile or toluene. As shown in Scheme 1, compounds of General Formula I can also be prepared by coupling heterocylic compounds of Formula IV where J is a trialkyltin (e.g. $Me_3Sn$), trialkylsilyl (e.g. $Me_3Si$), or boronic acid (e.g. $B(OH)_2$) moiety with aryl halides of Formula V where G is bromine or iodine using the same conditions as described above.

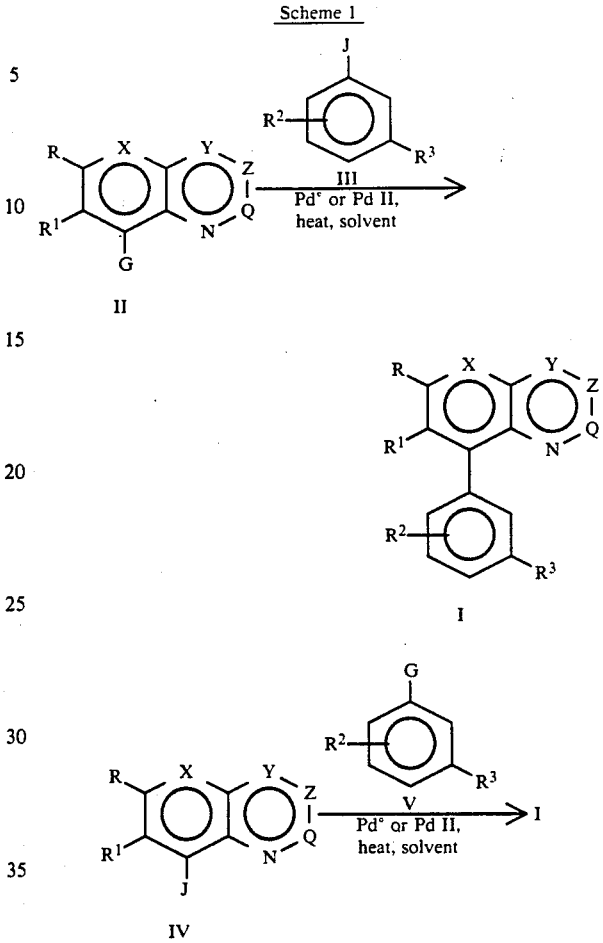

Scheme 1

Heterocycles of Formula II can be prepared by the methods summarized in Schemes 2-10 and Equations 1-5. By methods also reported in the above cited art, treatment of heterocycles of Formula II where G is hydrogen, bromine, or iodine with base such as n-butyl lithium followed by quenching with a trialkyltin halide, trialkylsilyl halide, or trialkyl borate gives heterocylic intermediates of Formula IV. Substituted aryl compounds of Formula III and V are either known or readily prepared by methods given in the above references.

As illustrated in Scheme 2, quinolines of Formula IIa and IIb can be prepared by reaction of anilines of Formula VI with substituted acroleins, vinyl ketones, and diketones of Formulas VIIa and VIId where $R^4$ and $R^8$ are hydrogen or alkyl, $R^5$ is haloalkyl, haloalkenyl, haloalkynyl, or halocycloalkyl and R, $R^1$, and G are as previously defined. By the methods of Skraup (*Chem. Ber.* 1880, 13, 2086; 1882, 15, 987) and Combs (*Compt. rend.* 1887, 106, 142; *Bull. Soc. Chim. France*, 1888, 49, 90), anilines VI can be heated neat with compounds VIIa and VIId followed by treatment with a strong inorganic acid such as sulfuric acid to give IIa and IIb.

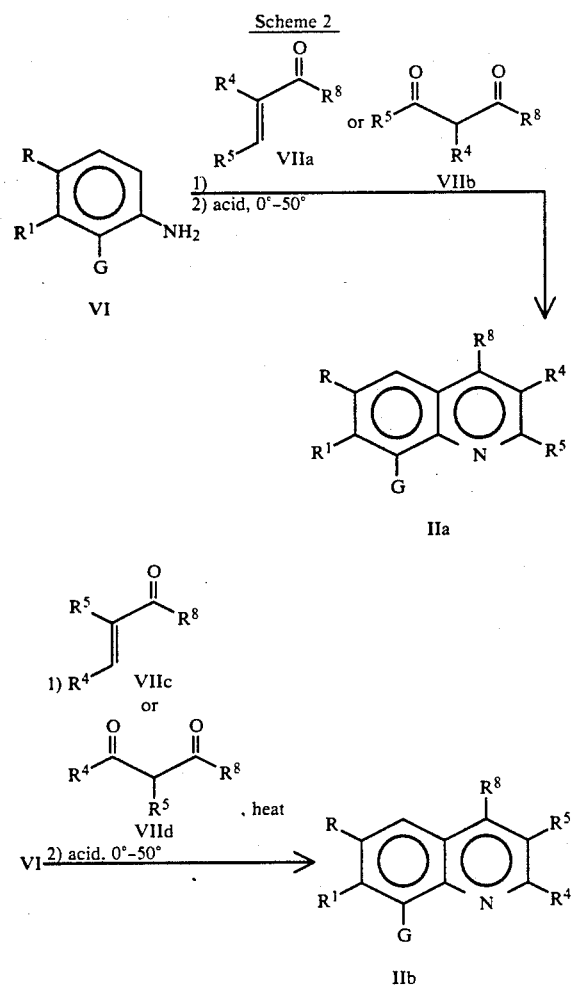

Scheme 3 illustrates the synthesis of quinolines IIa and IIc where $R^4$ and $R^8$ are hydrogen or alkyl, $R^5$ is $OR^6$, $SR^7$ or chlorine, and R, $R^1$, and G are as defined above. Reaction of anilines of Formula VI with substituted cinnamoyl chlorides of Formula VIIIa with a base such as pyridine with or without a solvent such as methylene chloride or tetrahydrofuran gives cinnamides of Formula VIIIb which can then be treated with an excess of a Lewis acid such as aluminum trichloride using the conditions of Johnston et al (*J. Chem. Soc. Perkin I* 1972, 1648) to give hydroxyquinolines of Formula VIIIc. Heating VIIIc in thionyl chloride or phosphorous oxychloride gives chloroquinolines IIc. Displacement of the chloro group with $R^6O^-M^+$ or $R^7S^-M^+$ (where M is an alkali or alkaline metal such as sodium, potassium, or lithium and $R^6$ and $R^7$ are as previously defined) affords quinolines IIa where $R^5$ is $OR^6$ or $SR^7$. Alkylation of VIIIc with $R^6L$ (where L is a leaving group such as halogen, e.g. bromine or chlorine) in the presence of a base such as triethylamine or sodium hydroxide can also give IIa where $R^5$ is $OR^6$. Reaction of VIIIc with phosphorous pentasulfide in a solvent such as pyridine affords mercaptopyridines of Formula VIIId which on alkylation with $R^7L$ (L is as described above) gives IIa where $R^5$ is $SR^7$. Oxidation of IIa where $R^5$ is $SR^7$ with an oxidizing agent such as meta-chloroperoxybenzoic acid gives quinolines of Formula IIa where $R^5$ is $S(O)R^7$ or $S(O)_2R^7$.

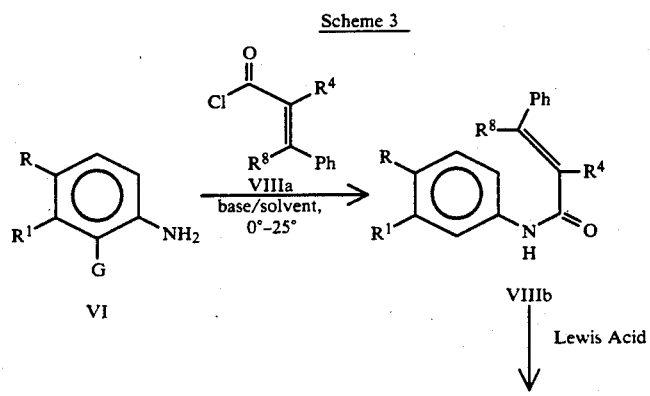

Scheme 3

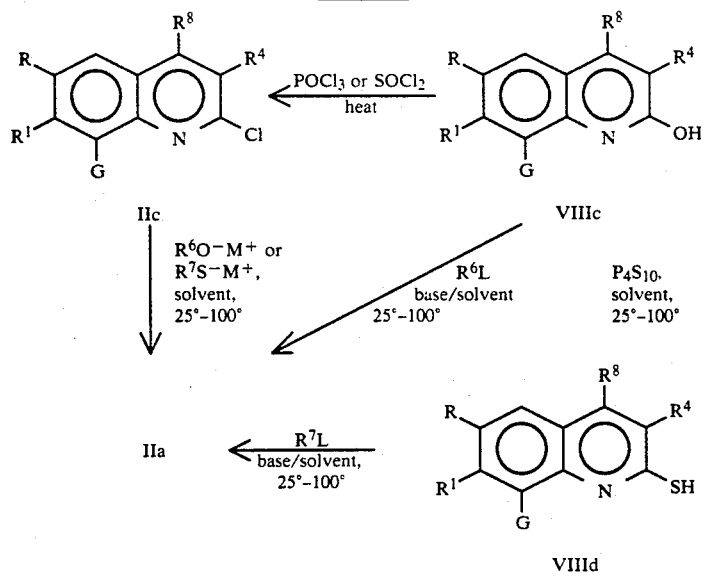

Quinolines of Formula IIb where $R^4$ is alkoxy or halogen and $R^5$ is haloalkyl, haloalkenyl, haloalkynyl, or cyclohaloalkyl, $R^8$ is hydrogen or alkyl and R, $R^1$, and G are as defined above can be made from the starting materials VI and cinnamoyl chlorides of Formula VIIIe (Equation 1) using the same chemistry as shown in Scheme 3.

Equation 1

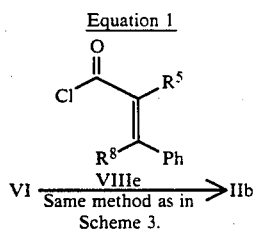

Quinoxalines and pyridopyrazines of Formula IId and IIe where X is CH or N, $R^4$ is hydrogen or alkyl, $R^5$ is haloalkyl, haloalkenyl, or haloalkynyl, and R, $R^1$, and G are as previously defined can be made by the procedure shown in Scheme 4.

Scheme 4

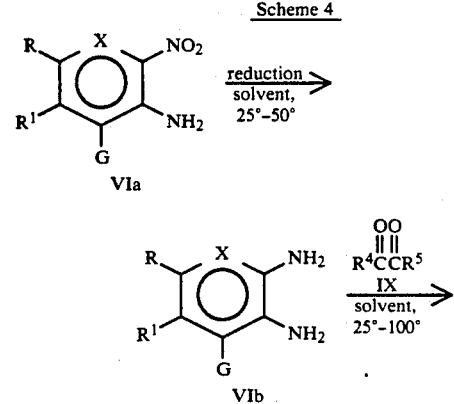

-continued
Scheme 4

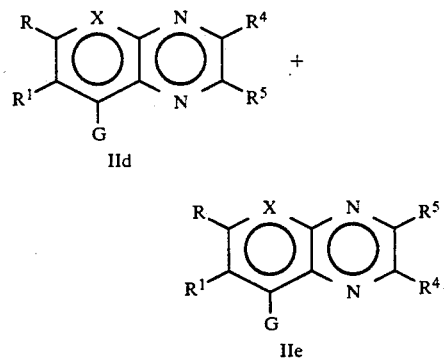

Reduction (e.g. catalylic hydrogenation with palladium on carbon in a solvent such as tetrahydrofuran or ethanol) of nitroanilines and nitropyridinyl amines of Formula VIa gives phenylenediamines and diaminopyridines of Formula VIb. By the methods related to that of Jones et al (*Org. Syntheses* 1950, 30, 86), Gabriel et al (*Chem. Ber.* 1907, 40, 4850), and Bottcher (*Chem. Ber.* 1913, 46, 3084), condensation of VIb with α-diketones and α-ketoaldehydes of Formula IX in a nonpolar or polar protic or aprotic solvent such as ethanol, water, or tetrahydrofuran affords heterocycles IId and IIe.

Schemes 5 and 6 illustrate the syntheses of quinoxalines and pyridopyrazines of Formula IId and IIe where $R^5$ is halogen, $OR^6$ or $SR^7$ and X, R, $R^1$, $R^4$, and G are defined as above. Condensation of compounds of Formula VIb with α-aldo and α-ketoesters of Formula IXa (Scheme 5) by a method similar to that of Hinsberg (*Chem. Ber.* 1884, 18, 1228) in a polar protic or aprotic solvent such as ethanol, water or tetrahydrofuran gives hydroxyheterocycles of Formula IXb and IXc. Ethyl ester analogs of IXa can also be readily used in this condensation. Treatment of these hydroxyheterocycles with thionyl chloride or phosphorous oxychloride gives the chloroheterocycles IIf and IIg. Displacement of the chloro substituent with $R^6O^-M^+$or $R^7S^-M^+$(where M is an alkali or alkaline metal such as sodium, potassium, or lithium) yields compounds IId and IIe (where $R^5$ is $OR^6$ or $SR^7$).

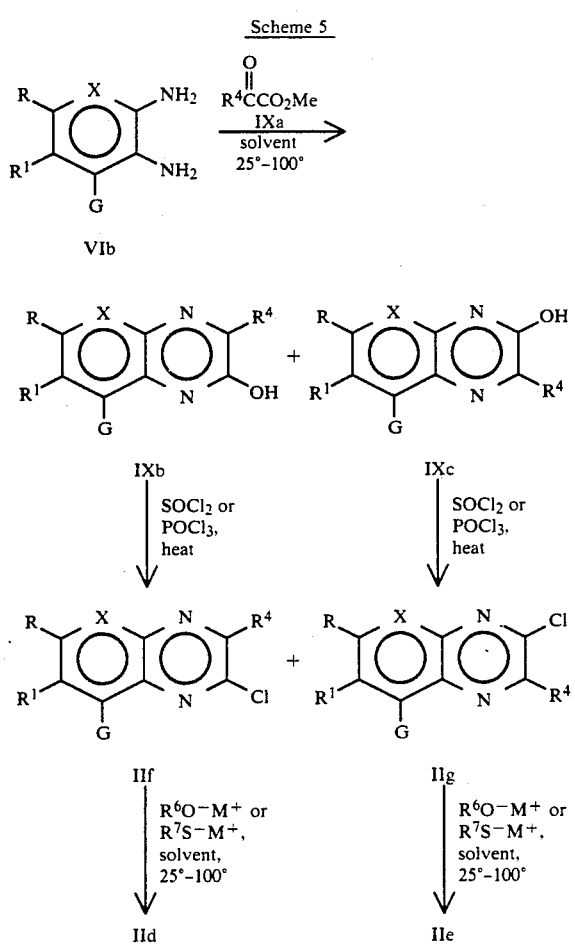

Scheme 6 demonstrates that hydroxyheterocycles IXb and IXc can also be converted to compounds IId and IIe using similar chemistry as that shown in Scheme 3. Preparation of compounds IId and IIe where $R^5$ is $R^7S$ involve making intermediate mercaptoheterocycles IXd and IXe.

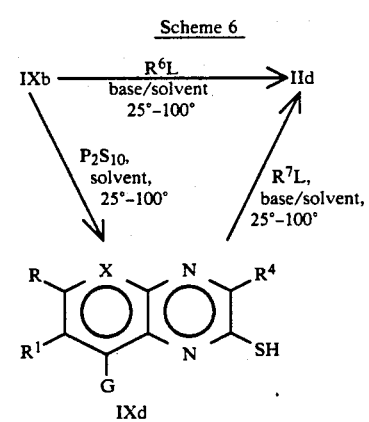

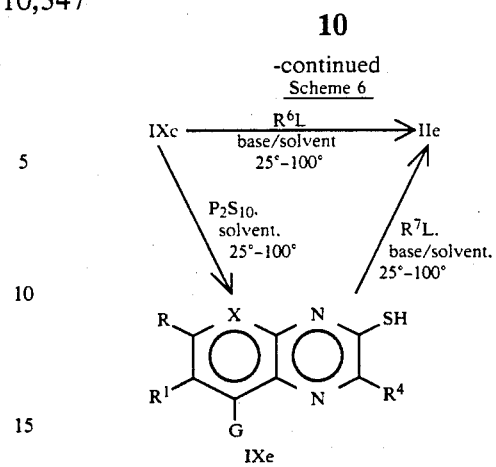

Equation 2 illustrates that compounds IId and IIe where $R^4$ is alkoxy and $R^5$ is haloalkyl, halocycloalkyl, haloalkenyl, or haloalkynyl and R, $R^1$, X, and G are as defined above can be made from the starting materials VIb and the α-ketoesters IXf using the same chemistry as that in Schemes 5 and 6.

Equation 2

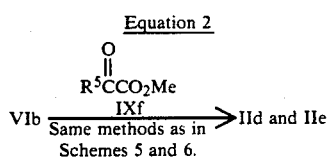

By a method similar to that reported by Reich et al (*J. Med. Chem.* 1989, 32, 2474), Scheme 7 summarizes the preparation of benzotriazines and pyridotriazines of Formula IIh where $R^5$ is haloalkyl, halocycloalkyl, haloalkenyl, or haloalkynyl and R, $R^1$, G, and X are as defined above. Reaction of nitrophenyl hyrazines and nitropyridinyl hydrazines of Formula X with an acid chloride of Formula Xa in a polar protic or aprotic solvent such as ethanol or acetonitrile gives hydrazide hydrochlorides of Formula Xb which can undergo catalytic hydrogenation using palladium on carbon or other suitable transition metal catalyst in a polar protic solvent such as ethanol followed by heating to give heterocycles of Formula Xc. Oxidation of Xc with an appropriate oxidizing agent in a suitable medium, e.g. manganese dioxide in aqueous sodium hydroxide or potassium ferricyanide in aqueous ammomium hydroxide, affords IIh.

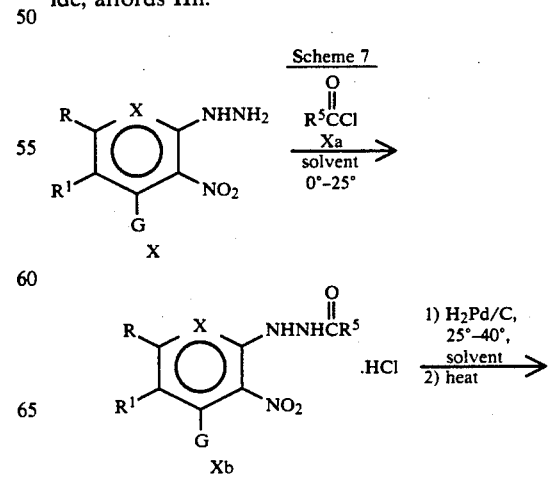

-continued
Scheme 7

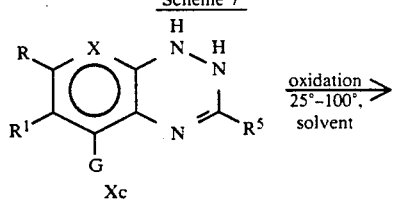

Xc

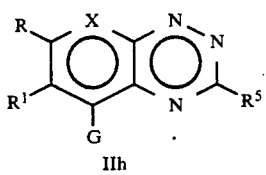

IIh

By the same technique demonstrated in Scheme 7, nitrophenyl hydrazines and nitropyridinyl hydrazines of Formula Xd (Equation 3) can be converted to heterocycles of Formula IIj which are regioisomeric with IIh.

Equation 3

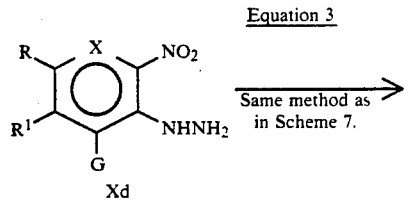

Xd

-continued
Equation 3

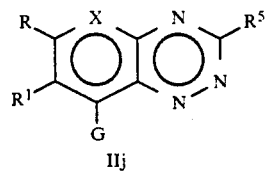

IIj

Scheme 8 illustrates the preparation of benzotriazines and pyridotriazines of Formula IIh and their N-oxides IIk and III where $R^5$ is halogen, $OR^6$, or $SR^7$ and R, $R^1$, X, and G are as previously defined. Using the conditions of Wolf et al (*J. Org. Chem.* 1954, 76, 3551), reaction of VIa with cyanamide in an acid medium such as a mixture of concentrated hydrochloric and acetic acid (extremely exothermic) followed by heating with aqueous base, e.g. sodium hydroxide, provides aminoheterocyclic N-oxides of Formula Xd. Diazotization with sodium nitrite in aqueous sulfuric acid gives hydroxyheterocycles Xe and diazotization in concentrated hydrochloric acid yields chloroheterocycles IIk. By chemistry previously discussed in Scheme 3, III can be obtained from both Xe and IIk. Reduction of the N-oxides III, e.g. catalytic hydrogenation over palladium, afford IIh. N-oxides III can also be coupled directly with III to give N-oxides of I.

Scheme 8

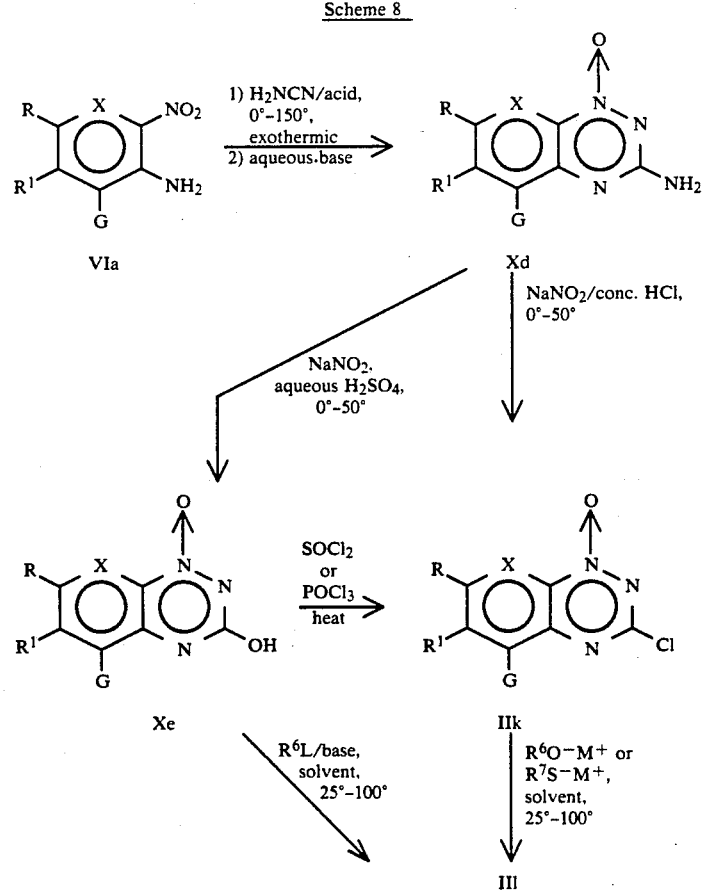

Scheme 8

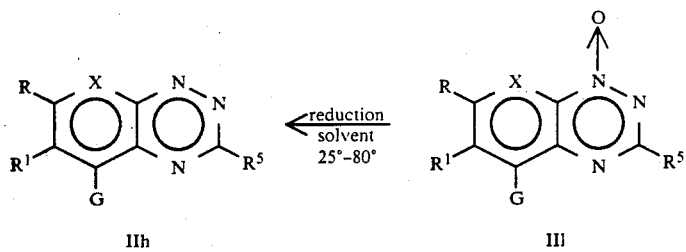

Regioisomeric benzotriazines and pyridotriazines of Formula IIj (Equation 4) and their N-oxides where $R^5$ is halogen, $OR^6$, or $SR^7$ and R, $R^1$, G, and X are as defined previously, can be obtained by starting with nitroanilines and nitropyridinylamines of Formula Xg and applying the chemistry shown in Scheme 8.

Equation 4

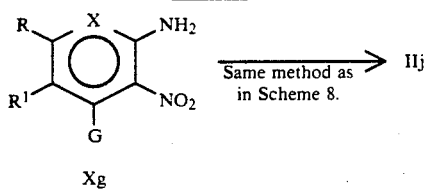

By the methods illustrated in Scheme 3, compounds Xe (Scheme 8) can be converted to compounds of Formula III as shown in Equation 5.

Equation 5

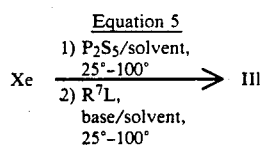

Scheme 9 demonstrates the Synthesis of heterocycles of Formula IIm and IIn (where $R^5$ is haloalkyl, halocycloalkyl, haloalkenyl, or haloalkynyl and other groups defined as indicated above) from amino compounds XI and anhydrides of Formula XIa. The chemistry is related to that described in previous schemes. Hydrogenolysis e.g. catalytic using palladium on carbon, or displacement with $R^8-M^+$ (where $R^8$ is alkoxy, CN, or alkyl) of the chloro group of IIm affords IIn where $R^8$ is hydrogen, alkoxy, CN, or alkyl.

Scheme 9

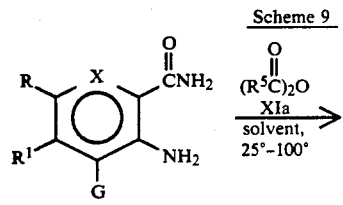

-continued
Scheme 9

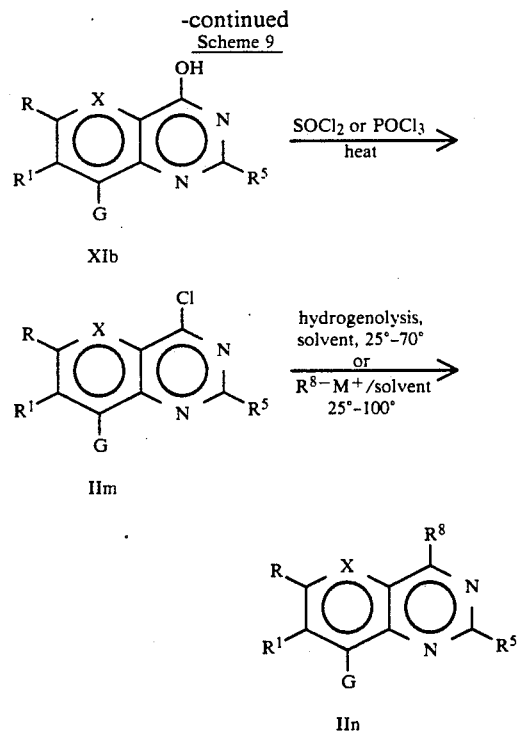

Preparation of compounds of Formula IIo, IIm, and IIn where $R^5$ is halogen, $OR^6$ or $SR^7$ and the remaining groups are as previously defined is shown in Scheme 10. The chemistry in Scheme 10 is similar to that described in previous schemes.

Scheme 10

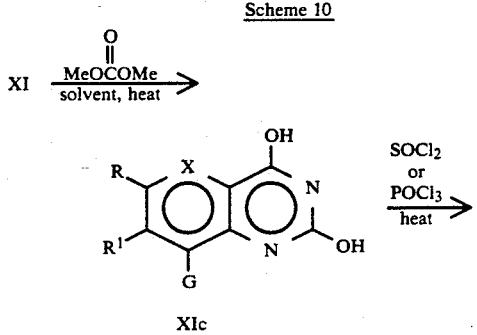

-continued
Scheme 10

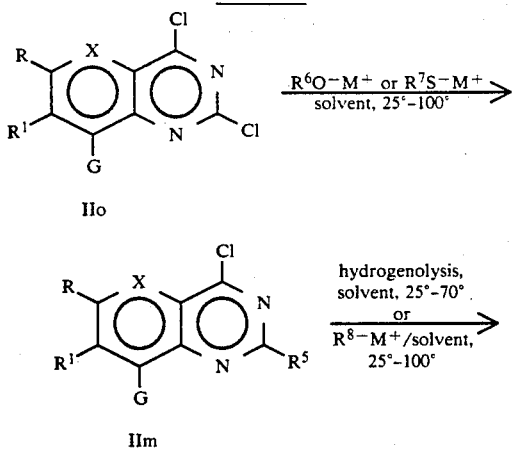

Cinnolines of Formula II where X is CH, Y is $CR^8$, Z is $CR^5$ and Q is N, (other substituents as previously defined) can be prepared by the methods reviewed by Elderfield (*Heterocyclic Compounds*, John Wiley & Sons, 1957, Volume 6, Chapter 5) and used in conjunction with procedures provided in the previous schemes.

N-oxides of compounds of Formula I can be made by treating compounds of Formula I with an oxidizing agent such as meta-peroxybenzoic acid in an appropriate solvent such as methylene chloride. Salts of Formula I can also be prepared by treating compounds of Formula I with a suitable acid such as hydrochloric acid.

EXAMPLE 1

Preparation of 3-(trifluoromethyl)phenyltrimethylstannane

To 20.0 g (88.9 mmol) of meta-bromobenzotrifluoride stirring in 200 ml of tetrahydrofuran at −78° C., 61.2 ml of 1.6M n-butyl lithium (97.9 mmol) in hexane was added dropwise. After stirring the reaction 10 minutes at −78° C., 19.5 g (97.8 mmol) of trimethyltin chloride dissolved in 30 ml of tetrahydrofuran was added dropwise and the mixture stirred for 10 minutes at −78° C. before allowing to warm to room temperature. The reaction mixture was quenched with excess saturated sodium bicarbonate and extracted with ethyl acetate (300 ml). The extract was washed with saturated sodium bicarbonate and brine, dried over magnesium sulfate, and evaporated in vacuo to give a crude yield of 20.2 g of the above product, isolated as a oily semi-solid. This aryl stannane was used directly as a crude material in the coupling reactions with heterocycles of Formula II.

EXAMPLE 2

Preparation of 6-Methyl-2-(2,2,2-trifluoroethoxy)-8-[3-(trifluoromethyl)phenyl]quinoline To 25.0 (134.4 mmol) of 2-bromo-4-methylaniline stirring in 100 ml of pyridine at 0° C., 29.1 g (174.7 mmol) of cinnamoyl chloride was added dropwise. The mixture was allowed to warm to room temperature and stirred as a thick suspension for 1 h. Methylene chloride (400 ml) and excess 5% hydrochloric acid was added. The organic layer was separated, washed with 5% hydrochloric acid (2X), water and brine, dried over magnesium sulfate, and evaporated in vacuo. To the residue, n-butyl chloride was added and a solid filtered and dried to give a 33.8 g yield of N-2-bromo-4-methylphenyl cinnamide, m.p. 148°-149° C. (ethyl acetate).

A mixture of 15.0 g (47.5 mmol) of the above prepared N-2-bromo-4-methylphenyl cinnamide and 18.9 g (142.1 mmol) of aluminum trichloride was heated as a melt at about 100° C. for 1.25 h. The viscous syrup was poured onto ice and the resulting aqueous mixture stirred 10 minutes and extracted with ethyl acetate (400 ml). The organic extract was washed with water, brine, dried over magnesium sulfate, and evaporated in vacuo. To the residue was added n-butyl chloride and 5.5 g of a crude solid (8-bromo-2-hydroxy-6-methylquinoline) was filtered, dried, and taken on directly to the next step without characterization.

A 5.0 g sample of the above solid and 35 ml of phosphorous oxychloride was heated at reflux for 30 minutes. The hot mixture was poured onto excess ice and the resulting aqueous mixture extracted with 300 ml of diethyl ether. The ether extract was separated and washed with water, brine, dried over magnesium sulfate, and evaporated in vacuo to give a dark oil. Silica gel column chromatography (5:1 followed by 3:1 hexane/ethyl acetate) afforded 1.8 g of 8-bromo-2-chloro-6-methylquinoline isolated as a solid, m.p. 107°-108° C. A second lower $R_f$ material (1.1 g) was also isolated on chromatography and identified as 2-chloro-6-methylquinoline, m.p. 109°-111° C.

To 0.8 g of 60% sodium hydride (oil dispersion) stirring in 20 ml of tetrahydrofuran at room temperature, 2.5 ml (34.3 mmol) of 2,2,2-trifluoroethanol was added dropwise. An exotherm occurred and to the resulting solution 1.7 g (6.7 mmol) of 8-bromo-2-chloro-6-methylquinoline was added followed by heating at reflux for 7 h. Ethyl acetate (200 ml) and excess water was added and the organic layer separated and washed with water and brine, dried over magnesium sulfate, and evaporated in vacuo to give an oil. Silica gel column chromatography (20:1 followed by 10:1 hexane/ethyl acetate) afforded 1.9 g of 8-bromo-6-methyl-2-(2,2,2-trifluoroethoxy)quinoline, m.p. 61°-62° C.

A mixture of 1.5 g (6.2 mmol) of 8-bromo-6-methyl-2-(2,2,2-trifluoroethoxy)quinoline, 2.3 g of crude 3-(trifluoromethyl)phenyltrimethylstannane (Example 1), and 0.2 g of tetrakis(triphenylphosphine)palladium(O) was heated in 30 ml of toluene at reflux with stirring for 3 hours. Ethyl acetate (200 ml) and excess water was added. The organic layer was separated, washed with water and brine, dried over magnesium sulfate, and evaporated in vacuo to give an oil. Silica gel column chromatography (20:1 followed by 10:1 hexane/ethyl acetate) afforded 0.7 g of product, isolated as an oil. NMR(CDCl3): ppm 2.55 (s, 3H), 4.71 (q, 2H), 7.15 (d, 1H), 7.5-8.15 (m, 7H).

EXAMPLE 3

Preparation of 6-Methyl-2-(2.2.2-trifluoroethoxy)-8-[3-(trifluoromethyl)phenyl]quinoxaline and 6-Methyl-3-(2,2,2-trifluoroethoxy)-8-[3-(trifluoromethyl)phenyl]quinoxaline A mixture of (92 mmol) of 2-bromo-4-methyl-6-nitroaniline and catalytic amount of 10% palladium on carbon in 120 ml of tetrahydrofuran was placed on a Paar hydrogenator for 6 h at room temperature at 50-40 psi. The reaction mixture was filtered through celite and to the filtrate was added dropwise 50.0 ml of 50% glyoxylic acid. The resulting suspension was stirred at room temperature overnight, the insoluble material filtered, washed with water and ethyl acetate, and oven dried to yield 8.5 g of a mixture of 8-bromo-2-hydroxy-6-methylquinoxaline and 8-bromo-3-hydroxy-6-methyl-quinoxaline.

A 5.0 g (20.9 mmol) sample of the above mixture of 2- and 3-hydroxyquinoxalines was heated in 30 ml of thionyl chloride containing a few drops of dimethylformamide. The reaction was heated at reflux for 1.5 h and the resulting solution, which gradually formed on heating, was poured carefully onto ice. The aqueous was extracted with ethyl acetate (250 ml) and the separated organic layer washed with water (2X) and brine, dried over magnesium sulfate, and yellow solid residue. Hexane was added and the mixture stirred several minutes before filtering to give,2.1 g of only 8-bromo-3-chloro-6-methylquinoxaline. Evaporating the hexane filtrate to dryness gave another 3.2 g of a crude solid which was roughly a 1:1 mixture of 8-bromo-2-chloro-6-methyl-quinoxaline and 8-bromo-3-chloro-6-methylquinoxaline.

To 0.46 g of 60% sodium hydride (oil dispersion) stirring in 20 ml of tetrahydrofuran, was added dropwise 1.54 ml of 2,2,2-trifluoroethanol followed by the addition of 1.8 g of the above crude mixture of quinoxalines. The reaction mixture was heated at reflux 45 minutes. Glacial acetic acid (2.0 ml) and excess water was added and the aqueous mixture extracted with ethyl acetate. The separated organic layer was washed with water, saturated sodium bicarbonate and brine, dried over magnesium sulfate, and evaporated in vacuo to give 2.4 g of an oily solid residue which was taken on directly to the next step.

A stirred mixture of 2.4 g of the above oily solid residue, 4.5 g of crude 3-(trifluoromethyl)-phenyl-trimethylstannane (Example 1), and 0.2 g of tetrakis(triphenylphosphine)palladium(0) was heated in 30 ml of toluene for 4 h. The reaction mixture was concentrated to dryness in vacuo and the residue flash chromatographed on silica gel (40:1 hexane/ethyl acetate) to give 0.7 g of 6-methyl-3-(2,2,2-trifluoroethoxy)-8-[3-(trifluoromethyl)phenyl]quinoxaline (first to elute, m.p. 114°-117° C.) and 0.8 g of 6-methyl-2-(2,2,2-trifluoroethoxy)-8-[3-(trifluoromethyl) phenyl]-quinoxaline (m.p. 46°-48° C.).

EXAMPLE 4

Preparation of
2-Methoxy-6-methyl-8-[3-(trifluoromethyl)phenyl]-quinoxaline and
3-Methoxy-6-methyl-8-[3-(trifluoromethyl)phenyl-quinoxaline To 2.3 g of a crude sample mixture of 8-bromo-2-chloro-6-methylquinoxaline and 8-bromo-3-chloro-6-methylquinoxaline (prepared as in Example 3) stirring in 20 ml of methanol, 6.3 ml of a 25 weight % of sodium methoxide in methanol was added and the mixture heated at reflux for 1 h. Glacial acetic acid (3.0 ml), 200 ml of ethyl acetate, and excess water was added. The separated organic layer was washed with saturated sodium bicarbonate, brine, dried over magnesium sulfate, and evaporated in vacuo to give 2.0 g of an oily solid residue which was taken on directly to the next step.

A stirred mixture of the above oily solid residue, 3.2 g of crude 3-(trifluoromethyl)phenyltrimethylstannane (Example 1), and 0.2 g of tetrakis(triphenylphosphine)palladium(0) were heated in 35 ml of toluene at reflux for 8 h. In vacuo, the reaction mixture was evaporated to dryness and the residue flash chromatographed on silica gel (1:1 hexane/n-butyl chloride followed by straight n-butyl chloride) to give 0.4 g of 3-methoxy-5-methyl-8-[3-(trifluoromethyl)phenyl]quinoxaline (first product isomer to elute, m.p. 141°-142° C.) and 0.5 g of 2-methoxy-5-methyl-8-[3-(trifluoromethyl)phenyl]-quinoxaline(m.p. 119°-121° C.).

EXAMPLE 5

Preparation of
2-(Difluoromethoxy)-6-methyl-8-[3-(trifluoromethyl)-phenyl]-quinoxaline and
3-(Difluoromethoxy)-6-methyl-8-[3-(trifluoromethyl)-phenyl]quinoxaline To a suspension of 5.0 g (20.9 mmol) of the above isomer mixture of 8-bromo-2-hydroxy-6-methylquinoxaline and 8-bromo-3-hydroxy-6-methylquinoxaline (prepared as in Example 3) and 9.0 g (27.1 mmol) of tetra-n-butylammonium bromide stirring in 150 ml of dioxane, 20 g (250.0 mmol) of 50% aqueous sodium hydroxide were added. The reaction mixture was placed under an atmosphere of chlorodifluoromethane (Freon-22®) whereby slight pressure was maintained by having a balloon over the reaction flask. A slow exotherm occurred and the mixture stirred 4 h. Excess water and 300 ml of diethyl ether were added. The separated organic extract was washed with water, brine, dried over magnesium sulfate, and evaporated in vacuo to give an oil residue which quickly solidified. Hexane was added, the mixture stirred several minutes, and filtered to give 3.1 g of 8-bromo-3-difluoromethoxy-6-methylquinoxaline. Evaporating the filtrate gave 2.5 g of a crude isomer mixture of 8-bromo-2-difluoromethoxy-6-methyl-quinoxaline and 8-bromo-3-difluoromethoxy-6-methyl-quinoxaline.

A stirred mixture of 1.5 g (5.2 mmol) of the above 2- and 3-difluoromethoxyquinoxaline isomer mixture, 4.0 g of crude 3-(trifluoromethyl)phenyltrimethylstannane (Example 1), and 0.2 g of tetrakis(triphenylphosphine)-palladium(0) was heated at reflux for 16 h. The reaction mixture was evaporated in vacuo and the residue flash chromatographed on silica gel (9:1 followed by 1:1 hexane/n-butyl chloride) to afford 0.51 g of 3-(difluoromethoxy)-6-methyl-8-[3-(trifluoromethyl)-phenyl]quinoxaline (first product isomer to elute, m.p. 105°-106° C.) and 0.4 g of 2-(difluoromethoxy)-6-methyl-8-[3-(trifluoromethyl)phenyl]quinoxaline (m.p. 103°-104° C.).

EXAMPLE 6

Preparation of
6-Methyl-2-(trifluoromethyl)-8-[3-(trifluoromethyl)-phenyl]quinoxaline and
6-Methyl-3-(trifluoromethyl-8-[3-(trifluoroomethyl)-phenyl]quinoxaline A mixture of 20.0 9 (B6.6 mmol) of 2-bromo-4-methyl-6-nitroaniline and a catalytic amount of 10% palladium on carbon in 100 ml of tetrahydrofuran was placed on a Paar hydrogenator at room temperature at 50-40 psi for 6 h. The reaction mixture was filtered through celite which was then washed with ethyl acetate. A total of 300 ml of ethyl acetate was added to the filtrate which was washed with water, brine, dried over magnesium sulfate and evaporated in vacuo to give a dark oily semi-solid. Flash column silica gel chromatography (methylene chloride followed by 2:1 hexane/ethyl acetate) afforded 17.0 g of the main component: 3-bromo-5-methyl-ortho-phenylenediamine. The chromatographed product, which still contained some minor impurities, was used directly in the next step. It was initially an dark oil which solidified.

To 10.0 g (37.0 mmol) of 1,1-dibromo-3,3,3-trifluoroacetone stirring in 50 ml of water, 8.0 g (97.6 mmol) of anhydrous sodium acetate was added and the stirred mixture heated near reflux for 45 minutes followed by stirring at ambient temperature for 30 minutes. A 4.0 g (20.0 mmol) sample of the above phenylenediamine was added and the mixture stirred 2 h. Excess water and 250 ml of ethyl acetate was added and the separated organic extract washed with 5% hydrochloric acid, brine, dried over magnesium sulfate, and evaporated in vacuo to give dark oil. Flash column silica gel chromatography (40:1 followed by 30:1 hexane/ethyl acetate) afforded 4.3 g of a mixture (two close migrating spots) of 8-bromo-6-methyl-2-trifluoromethylquinoxaline and 8-bromo-6-methyl-3-trifluoromethylquinoxaline, isolated as a solid which melted at 69°-71° C.

A stirred mixture of 2.0 g (6.9 mmol) of the above quinoxaline isomers, 4.2 g of crude 3-(trifluoromethyl)-phenyltrimethylstannane, and 0.2 g of tetrakis(triphenylphosphine)palladium(0) were heated in 30 ml of toluene for 6 h. Additional stannane (about 0.5 g) and palladium catalyst (0.1 g) were added and the reaction heated another 6 h. The reaction mixture was evaporated in vacuo to dryness and the residue flash chromatographed (4:1 followed by 1:1 hexane/n-butyl chloride followed in turn by 100% n-butyl chloride) to afford 0.2 g of 6-methyl-3-(trifluoromethyl)-8-[3-(trifluoromethyl)-phenyl]quinoxaline (first product isomer to elute, m.p. 93°-94° C.) and 1.08 g of 6-methyl-2-(trifluoromethyl)-8-[3-(trifluoromethyl)phenyl]quinoxaline (m.p. 117°-118° C.).

EXAMPLE 7

7-Methyl-3-(2,2,2-trifluoroethoxy)-5-[3-(trifluoromethyl)phenyl]-1,2,4-benzotriazine-1-oxide and 7-Methyl-3-(2,2,2-trifluoroethoxy)-5-[3-trifluoromethyl)phenyl]-1,2,4-benzotriazine To 13.0 g (56.3 mmol) of 2-bromo-4-methyl-6-nitroaniline stirring in a mixture of 25 ml glacial acetic acid and 5 ml of concentrated hydrochloric acid at 80° C., 29.0 g (690.5 mmol) of cyanamide and 25 ml of concentrated hydrochloric acid were added simultaneously, separately, and very slowly. At one point during the addition, a vigorous exotherm occurred and the external heat immediately removed. After the addition, the reaction was heated at reflux for 15 minutes. On cooling to about 50° C., 100 ml of 25% aqueous sodium hydroxide were added dropwise and the mixture heated at reflux 15 minutes. The reaction was cooled to room temperature, the insoluble orange solid filtered and washed with water followed by ethyl acetate to afford 7.4 g of yellow 3-amino-5-bromo-7-methyl-1,2,4-benzotriazine-1-oxide after drying.

Sodium nitrite (7.0 g, 101.4 mmol) was added portionwise to a suspension of 7.0 g (27.5 mmol) of the above aminobenzotriazine-N-oxide stirring in 140 ml of concentrated hydrochloric acid at ambient temperature. The mixture was stirred overnight and heated at 60° C. for 2 h. Excess water and 400 ml of ethyl acetate were added and the separated organic layer washed with water, saturated sodium bicarbonate, brine, and dried over magnesium sulfate. Some insoluble starting aminoheterocycle was present during the extractive workup but was not attempted to be removed. Evaporating the organic extract to dryness in vacuo afforded a crude yellow solid residue which was flash chromatographed on silica gel (4:1 methylene chloride/hexane) to give 2.5 g of 5-bromo-3-chloro-7-methyl-1,2,4-benzotriazine-1-oxide, m.p. 207°-209° C.

To 0.5 g of 60% sodium hydride stirring in 30 ml of tetrahydrofuran, 3.0 ml of 2,2,2-trifluoroethanol was added dropwise at ambient temperature. A solution resulted and 2.0 g (7.29 mmol) of the above 5-bromo-3-chloro-7-methyl-1,2,4-benzotriazine-1-oxide was added and at ambient temperature and the mixture stirred 2 h. Ethyl acetate (200 ml) and excess water were added and the separated organic extract washed with water, brine, and dried over magnesium sulfate. The solvent was removed in vacuo, hexane added to the residue, and the suspended yellow solid filtered and dried to afford 1.7 g of 5-bromo-7-methyl-3-(2,2,2-trifluoroethoxy)-1,2,4-benzotriazine-1-oxide, m.p. 127°-128° C.

A stirred mixture of 1.3 g (3.84 mmol) of the above benzotriazine N-oxide, 1.4 g of crude 3-(trifluoromethyl)phenyltrimethylstannane, and 0.2 g of tetrakis(triphenylphosphine)palladium(0) were heated in 35 ml of toluene at reflux for 4 h. The reaction mixture was evaporated in vacuo to dryness and the residue flashed chromatographed on silica gel (1:1 hexane/n-butyl chloride followed by 100% n-butyl chloride) to give 0.8 g of 7-methyl-3-(2,2,2-trifluoroethoxy)-5-[3-(trifluoromethyl)phenyl]1,2,4-benzotriazine-1-oxide (m.p. 168°-169° C.) and 0.24 g of 7-methyl-3-(2,2,2-trifluoroethoxy)-5-[3-(trifluoromethyl)phenyl]-1,2,4-benzotriazine (m.p. 140°-141°).

Using the procedures outlined in Schemes 1–10, Equations 1–5, and Examples 1–7, the compounds of Tables I–VIII and the Table of Compounds can readily be prepared by one skilled in the art.

TABLE I

Ia

| X | R | $R^1$ | $R^2$ | $R^3$ | $R^4$ | $R^5$ | $R^8$ |
|---|---|---|---|---|---|---|---|
| CH | Me | H | H | $CF_3$ | H | $CF_3$ | H |
| CH | Et | H | H | $CF_3$ | H | $CF_3$ | H |
| CH | n-Pr | H | H | $CF_3$ | H | $CF_3$ | H |
| CH | Me | H | H | $OCF_3$ | H | $CF_3$ | H |
| CH | Et | H | H | $OCF_3$ | H | $CF_3$ | H |
| CH | n-Pr | H | H | $OCF_3$ | H | $CF_3$ | H |
| CH | Me | H | H | $OCHF_2$ | H | $CF_3$ | H |
| CH | Me | H | H | $OCF_3$ | H | $OCHF_2$ | H |
| CH | Me | H | H | $CF_3$ | H | $OCHF_2$ | H |
| CH | Me | F | H | $CF_3$ | H | $CF_3$ | H |
| CH | Me | H | 6-F | $CF_3$ | H | $CF_3$ | H |
| CH | Me | H | 4-F | $CF_3$ | H | $CF_3$ | H |
| CH | Me | H | 2-OMe | $CF_3$ | H | $CF_3$ | H |
| CH | Me | H | 2-$CF_3$ | H | H | $CF_3$ | H |
| CH | Me | H | H | Cl | H | $CF_3$ | H |
| CH | Me | H | H | Br | H | $CF_3$ | H |
| CH | Me | H | H | CN | H | $CF_3$ | H |
| CH | Et | H | H | $CF_3$ | H | $OCHF_2$ | H |
| CH | Et | H | H | CN | H | $CF_3$ | H |
| CH | Me | H | H | $SCF_3$ | H | $CF_3$ | H |

TABLE I-continued

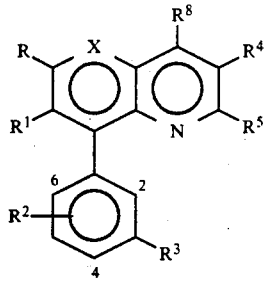

Ia

| X | R | R¹ | R² | R³ | R⁴ | R⁵ | R⁸ |
|---|---|----|----|----|----|----|----|
| CH | Me | H | H | H | H | $CF_3$ | H |
| CH | Me | H | H | $CF_3$ | H | $OCH_2CF_3$ | H |
| CH | Me | H | H | $CF_3$ | H | $SCF_3$ | H |
| CH | Me | H | H | $CF_3$ | H | OMe | H |
| CH | Et | H | H | $CF_3$ | H | OEt | H |
| CH | Me | H | H | $CF_3$ | H | $OCHMe_2$ | H |
| CH | Me | H | H | $CF_3$ | H | SMe | H |
| CH | Me | H | H | $CF_3$ | H | $CHF_2$ | H |
| CH | Et | H | H | $CF_3$ | H | $CHF_2$ | H |
| CH | Me | H | H | $OCF_3$ | H | $CHF_2$ | H |
| CH | Me | H | H | $CF_3$ | H | $OCF_2CHF_2$ | H |
| CH | Me | H | H | $CF_3$ | H | Cl | H |
| CH | MeCH=CH | H | H | $CF_3$ | H | $CF_3$ | H |
| CH | Me | H | H | $CF_3$ | H | $CH=CHCF_3$ | H |
| CH | Me | H | H | $CF_3$ | H | $OCHF_2$ | H |
| CH | Et | H | H | $CF_3$ | H | $OCHF_2$ | H |
| CH | $MeOCH_2$ | H | H | $CF_3$ | H | $CF_3$ | H |
| CH | $Me_2N$ | H | H | $CF_3$ | H | $CF_3$ | H |
| CH | MeNH | H | H | $CF_3$ | H | $CF_3$ | H |
| CH | Me | H | H | OMe | H | $CF_3$ | H |
| CH | Me | H | H | $CF_3$ | H | $SCHF_2$ | H |
| CH | Me | H | H | $CF_3$ | H | $SO_2CHF_2$ | H |
| CH | MeO | H | H | $CF_3$ | H | $CF_3$ | H |
| CH | MeS | H | H | $CF_3$ | H | $CF_3$ | H |
| CH | Me | H | H | $CF_3$ | Me | $CF_3$ | H |
| CH | Me | H | H | $CF_3$ | CN | $CF_3$ | H |
| CH | Me | H | H | $CF_3$ | OMe | $CF_3$ | H |
| CH | Me | H | H | $CF_3$ | Cl | $CF_3$ | H |
| N | Me | H | H | $CF_3$ | H | $CF_3$ | H |
| N | Et | H | H | $CF_3$ | H | $CF_3$ | H |
| N | Me | H | H | $CF_3$ | H | $OCHF_2$ | H |
| N | Et | H | H | $CF_3$ | H | $OCHF_2$ | H |
| N | Me | H | H | $OCF_3$ | H | $CF_3$ | H |
| N | Me | H | H | $OCHF_2$ | H | $CF_3$ | H |
| N | Me | H | H | CN | H | $CF_3$ | H |
| N | Et | H | H | CN | H | $CF_3$ | H |
| N | Me | H | H | $OCF_3$ | H | $OCHF_2$ | H |
| N | Me | H | H | $CF_3$ | H | OMe | H |
| N | Me | H | H | $SCF_3$ | H | $CF_3$ | H |
| CH | Me | H | H | $CF_3$ | H | $CF_3$ | Me |
| CH | Me | H | H | $CF_3$ | H | $CF_3$ | OMe |
| CH | Me | H | H | $CF_3$ | H | $CF_3$ | Cl |
| CH | Me | H | H | $CF_3$ | H | $CF_3$ | CN |

TABLE II

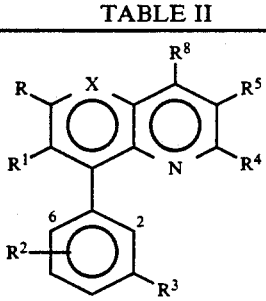

Ib

| X | R | R¹ | R² | R³ | R⁴ | R⁵ | R⁸ |
|---|---|----|----|----|----|----|----|
| CH | Me | H | H | $CF_3$ | H | $CF_3$ | H |
| CH | Et | H | H | $CF_3$ | H | $CF_3$ | H |
| CH | n-Pr | H | H | $CF_3$ | H | $CF_3$ | H |

TABLE II-continued

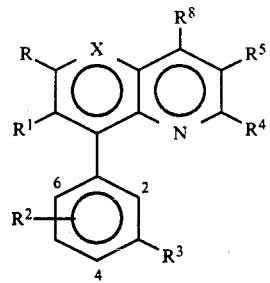

Ib

| X | R | R¹ | R² | R³ | R⁴ | R⁵ | R⁸ |
|---|---|----|----|----|----|----|----|
| CH | Me | H | H | $OCF_3$ | H | $CF_3$ | H |
| CH | Et | H | H | $OCF_3$ | H | $CF_3$ | H |
| CH | n-Pr | H | H | $OCF_3$ | H | $CF_3$ | H |
| CH | Me | H | H | $OCHF_2$ | H | $CF_3$ | H |
| CH | Me | H | H | $OCF_3$ | H | $OCHF_2$ | H |
| CH | Me | H | H | $CF_3$ | H | $OCHF_2$ | H |
| CH | Me | F | H | $CF_3$ | H | $CF_3$ | H |
| CH | Me | H | 6-F | $CF_3$ | H | $CF_3$ | H |
| CH | Me | H | 4-F | $CF_3$ | H | $CF_3$ | H |
| CH | Me | H | 2-OMe | $CF_3$ | H | $CF_3$ | H |
| CH | Me | H | 2-$CF_3$ | H | H | $CF_3$ | H |
| CH | Me | H | H | Cl | H | $CF_3$ | H |
| CH | Me | H | H | Br | H | $CF_3$ | H |
| CH | Et | H | H | $CF_3$ | H | $OCHF_2$ | H |
| CH | Me | H | H | CN | H | $CF_3$ | H |
| CH | Et | H | H | CN | H | $CF_3$ | H |
| CH | Me | H | H | $SCF_3$ | H | $CF_3$ | H |
| CH | Me | H | H | H | H | $CF_3$ | H |
| CH | Me | H | H | $CF_3$ | H | $OCH_2CF_3$ | H |
| CH | Me | H | H | $CF_3$ | H | $SCF_3$ | H |
| CH | Me | H | H | $CF_3$ | H | OMe | H |
| CH | Et | H | H | $CF_3$ | H | OEt | H |
| CH | Me | H | H | $CF_3$ | H | $OCHMe_2$ | H |
| CH | Me | H | H | $CF_3$ | H | SMe | H |
| CH | Me | H | H | $CF_3$ | H | $CHF_2$ | H |
| CH | Et | H | H | $CF_3$ | H | $CHF_2$ | H |
| CH | Me | H | H | $OCF_3$ | H | $CHF_2$ | H |
| CH | Me | H | H | $CF_3$ | H | $OCF_2CHF_2$ | H |
| CH | Me | H | H | $CF_3$ | H | Cl | H |
| CH | MeCH=CH | H | H | $CF_3$ | H | $CF_3$ | H |
| CH | Me | H | H | $CF_3$ | H | $CH=CHCF_3$ | H |
| CH | Me | H | H | $CF_3$ | H | $OCHF_2$ | H |
| CH | Et | H | H | $CF_3$ | H | $OCHF_2$ | H |
| CH | $MeOCH_2$ | H | H | $CF_3$ | H | $CF_3$ | H |
| CH | $Me_2N$ | H | H | $CF_3$ | H | $CF_3$ | H |
| CH | MeNH | H | H | $CF_3$ | H | $CF_3$ | H |
| CH | Me | H | H | OMe | H | $CF_3$ | H |
| CH | Me | H | H | $CF_3$ | H | $SCHF_2$ | H |
| CH | Me | H | H | $CF_3$ | H | $SO_2CHF_2$ | H |
| CH | MeO | H | H | $CF_3$ | H | $CF_3$ | H |
| CH | MeS | H | H | $CF_3$ | H | $CF_3$ | H |
| CH | Me | H | H | $CF_3$ | Me | $CF_3$ | H |
| CH | Me | H | H | $CF_3$ | CN | $CF_3$ | H |
| CH | Me | H | H | $CF_3$ | OMe | $CF_3$ | H |
| CH | Me | H | H | $CF_3$ | Cl | $CF_3$ | H |
| N | Me | H | H | $CF_3$ | H | $CF_3$ | H |
| N | Et | H | H | $CF_3$ | H | $CF_3$ | H |
| N | Me | H | H | $CF_3$ | H | $OCHF_2$ | H |
| N | Et | H | H | $CF_3$ | H | $OCHF_2$ | H |
| N | Me | H | H | $OCF_3$ | H | $CF_3$ | H |
| N | Me | H | H | $OCHF_2$ | H | $CF_3$ | H |
| N | Me | H | H | CN | H | $CF_3$ | H |
| N | Et | H | H | CN | H | $CF_3$ | H |
| N | Me | H | H | $OCF_3$ | H | $OCHF_2$ | H |
| N | Me | H | H | $CF_3$ | H | OMe | H |
| N | Me | H | H | $SCF_3$ | H | $CF_3$ | H |
| CH | Me | H | H | $CF_3$ | H | $CF_3$ | Me |
| CH | Me | H | H | $CF_3$ | H | $CF_3$ | OMe |
| CH | Me | H | H | $CF_3$ | H | $CF_3$ | Cl |
| CH | Me | H | H | $CF_3$ | H | $CF_3$ | CN |

TABLE III

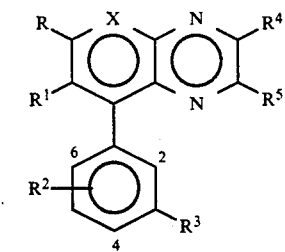 Ic

| X | R | R¹ | R² | R³ | R⁴ | R⁵ |
|---|---|---|---|---|---|---|
| CH | Me | H | H | CF₃ | H | CF₃ |
| CH | Et | H | H | CF₃ | H | CF₃ |
| CH | n-Pr | H | H | CF₃ | H | CF₃ |
| CH | Me | H | H | OCF₃ | H | CF₃ |
| CH | Et | H | H | OCF₃ | H | CF₃ |
| CH | n-Pr | H | H | OCF₃ | H | CF₃ |
| CH | Me | H | H | OCHF₂ | H | CF₃ |
| CH | Me | H | H | OCF₃ | H | OCHF₂ |
| CH | Me | H | H | CF₃ | H | OCHF₂ |
| CH | Me | F | H | CF₃ | H | CF₃ |
| CH | Me | H | 6-F | CF₃ | H | CF₃ |
| CH | Me | H | 4-F | CF₃ | H | CF₃ |
| CH | Me | H | 2-OMe | CF₃ | H | CF₃ |
| CH | Me | H | 2-CF₃ | H | H | CF₃ |
| CH | Me | H | H | Cl | H | CF₃ |
| CH | Et | H | H | CF₃ | H | OCHF₂ |
| CH | Me | H | H | Br | H | CF₃ |
| CH | Me | H | H | CN | H | CF₃ |
| CH | Et | H | H | CN | H | CF₃ |
| CH | Me | H | H | SCF₃ | H | CF₃ |
| CH | Me | H | H | H | H | CF₃ |
| CH | Me | H | H | CF₃ | H | OCH₂CF₃ |
| CH | Me | H | H | CF₃ | H | SCF₃ |
| CH | Me | H | H | CF₃ | H | OMe |
| CH | Et | H | H | CF₃ | H | OEt |
| CH | Me | H | H | CF₃ | H | OCHMe₂ |
| CH | Me | H | H | CF₃ | H | SMe |
| CH | Me | H | H | CF₃ | H | CHF₂ |
| CH | Et | H | H | CF₃ | H | CHF₂ |
| CH | Me | H | H | OCF₃ | H | CHF₂ |
| CH | Me | H | H | CF₃ | H | OCF₂CHF₂ |
| CH | Me | H | H | CF₃ | H | Cl |
| CH | MeCH=CH | H | H | CF₃ | H | CF₃ |
| CH | Me | H | H | CF₃ | H | CH=CHCF₃ |
| CH | Me | H | H | CF₃ | H | OCHF₂ |
| Et | H | H | CF₃ | H | OCHF₂ | |
| CH | Et | H | H | CF₃ | H | CF₃ |
| CH | Me₂N | H | H | CF₃ | H | CF₃ |
| CH | MeNH | H | H | CF₃ | H | CF₃ |
| CH | Me | H | H | OMe | H | CF₃ |
| CH | Me | H | H | CF₃ | H | SCHF₂ |
| CH | Me | H | H | CF₃ | H | SO₂CHF₂ |
| CH | MeO | H | H | CF₃ | H | CF₃ |
| CH | MeS | H | H | CF₃ | H | CF₃ |
| CH | Me | H | H | CF₃ | Me | CF₃ |
| CH | Me | H | H | CF₃ | CN | CF₃ |
| CH | Me | H | H | CF₃ | OMe | CF₃ |
| CH | Me | H | H | CF₃ | Cl | CF₃ |
| N | Me | H | H | CF₃ | H | CF₃ |
| N | Et | H | H | CF₃ | H | CF₃ |
| N | Me | H | H | CF₃ | H | OCHF₂ |
| N | Et | H | H | CF₃ | H | OCHF₂ |
| N | Me | H | H | OCF₃ | H | CF₃ |
| N | Me | H | H | OCHF₂ | H | CF₃ |
| N | Me | H | H | CN | H | CF₃ |
| N | Et | H | H | CN | H | CF₃ |
| N | Me | H | H | OCF₃ | H | OCHF₂ |
| N | Me | H | H | CF₃ | H | OMe |
| N | Me | H | H | SCF₃ | H | CF₃ |

TABLE IV

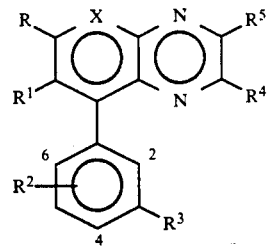 Id

| X | R | R¹ | R² | R³ | R⁴ | R⁵ |
|---|---|---|---|---|---|---|
| CH | Me | H | H | CF₃ | H | CF₃ |
| CH | Et | H | H | CF₃ | H | CF₃ |
| CH | n-Pr | H | H | CF₃ | H | CF₃ |
| CH | Me | H | H | OCF₃ | H | CF₃ |
| CH | Et | H | H | OCF₃ | H | CF₃ |
| CH | n-Pr | H | H | OCF₃ | H | CF₃ |
| CH | Me | H | H | OCHF₂ | H | CF₃ |
| CH | Me | H | H | OCF₃ | H | OCHF₂ |
| CH | Me | H | H | CF₃ | H | OCHF₂ |
| CH | Me | F | H | CF₃ | H | CF₃ |
| CH | Me | H | 6-F | CF₃ | H | CF₃ |
| CH | Me | H | 4-F | CF₃ | H | CF₃ |
| CH | Me | H | 2-OMe | CF₃ | H | CF₃ |
| CH | Me | H | 2-CF₃ | H | H | CF₃ |
| CH | Me | H | H | Cl | H | CF₃ |
| CH | Me | H | H | Br | H | CF₃ |
| CH | Et | H | H | CF₃ | H | OCHF₂ |
| CH | Me | H | H | CN | H | CF₃ |
| CH | Et | H | H | CN | H | CF₃ |
| CH | Me | H | H | SCF₃ | H | CF₃ |
| CH | Me | H | H | H | H | CF₃ |
| CH | Me | H | H | CF₃ | H | OCH₂CF₃ |
| CH | Me | H | H | CF₃ | H | SCF₃ |
| CH | Me | H | H | CF₃ | H | OMe |
| CH | Et | H | H | CF₃ | H | OEt |
| CH | Me | H | H | CF₃ | H | OCHMe₂ |
| CH | Me | H | H | CF₃ | H | SMe |
| CH | Me | H | H | CF₃ | H | CHF₂ |
| CH | Et | H | H | CF₃ | H | CHF₂ |
| CH | Me | H | H | OCF₃ | H | CHF₂ |
| CH | Me | H | H | CF₃ | H | OCF₂CHF₂ |
| CH | Me | H | H | CF₃ | H | Cl |
| CH | MeCH=CH | H | H | CF₃ | H | CF₃ |
| CH | Me | H | H | CF₃ | H | CH=CHCF₃ |
| CH | Me | H | H | CF₃ | H | OCHF₂ |
| CH | Et | H | H | CF₃ | H | OCHF₂ |
| CH | MeOCH₂ | H | H | CF₃ | H | CF₃ |
| CH | Me₂N | H | H | CF₃ | H | CF₃ |
| CH | MeNH | H | H | CF₃ | H | CF₃ |
| CH | Me | H | H | OMe | H | CF₃ |
| CH | Me | H | H | CF₃ | H | SCHF₂ |
| CH | Me | H | H | CF₃ | H | SO₂CHF₂ |
| CH | MeO | H | H | CF₃ | H | CF₃ |
| CH | MeS | H | H | CF₃ | H | CF₃ |
| CH | Me | H | H | CF₃ | Me | CF₃ |
| CH | Me | H | H | CF₃ | CN | CF₃ |
| CH | Me | H | H | CF₃ | OMe | CF₃ |
| CH | Me | H | H | CF₃ | Cl | CF₃ |
| N | Me | H | H | CF₃ | H | CF₃ |
| N | Et | H | H | CF₃ | H | CF₃ |
| N | Me | H | H | CF₃ | H | OCHF₂ |
| N | Et | H | H | CF₃ | H | OCHF₂ |
| N | Me | H | H | OCF₃ | H | CF₃ |
| N | Me | H | H | OCHF₂ | H | CF₃ |
| N | Me | H | H | CN | H | CF₃ |
| N | Et | H | H | CN | H | CF₃ |
| N | Me | H | H | OCF₃ | H | OCHF₂ |
| N | Me | H | H | CF₃ | H | OMe |
| N | Me | H | H | SCF₃ | H | CF₃ |

TABLE V

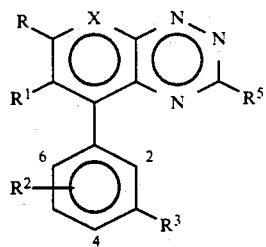

Ie

| X | R | R¹ | R² | R³ | R⁵ |
|---|---|---|---|---|---|
| CH | Me | H | H | $CF_3$ | $CF_3$ |
| CH | Et | H | H | $CF_3$ | $CF_3$ |
| CH | n-Pr | H | H | $CF_3$ | $CF_3$ |
| CH | Me | H | H | $OCF_3$ | $CF_3$ |
| CH | Et | H | H | $OCF_3$ | $CF_3$ |
| CH | n-Pr | H | H | $OCF_3$ | $CF_3$ |
| CH | Me | H | H | $OCHF_2$ | $CF_3$ |
| CH | Me | H | H | $OCF_3$ | $OCHF_2$ |
| CH | Me | H | H | $CF_3$ | $OCHF_2$ |
| CH | Me | F | H | $CF_3$ | $CF_3$ |
| CH | Me | H | 6-F | $CF_3$ | $CF_3$ |
| CH | Me | H | 4-F | $CF_3$ | $CF_3$ |
| CH | Me | H | 2-OMe | $CF_3$ | $CF_3$ |
| CH | Me | H | 2-$CF_3$ | H | $CF_3$ |
| CH | Me | H | H | Cl | $CF_3$ |
| CH | Et | H | H | $CF_3$ | $OCHF_2$ |
| CH | Me | H | H | Br | $CF_3$ |
| CH | Me | H | H | CN | $CF_3$ |
| CH | Et | H | H | CN | $CF_3$ |
| CH | Me | H | H | $SCF_3$ | $CF_3$ |
| CH | Me | H | H | H | $CF_3$ |
| CH | Me | H | H | $CF_3$ | $OCH_2CF_3$ |
| CH | Me | H | H | $CF_3$ | $SCF_3$ |
| CH | Me | H | H | $CF_3$ | OMe |
| CH | Et | H | H | $CF_3$ | OEt |
| CH | Me | H | H | $CF_3$ | $OCHMe_2$ |
| CH | Me | H | H | $CF_3$ | SMe |
| CH | Me | H | H | $CF_3$ | $CHF_2$ |
| CH | Et | H | H | $CF_3$ | $CHF_2$ |
| CH | Me | H | H | $OCF_3$ | $CHF_2$ |
| CH | Me | H | H | $CF_3$ | $OCF_2CHF_2$ |
| CH | Me | H | H | $CF_3$ | Cl |
| CH | MeCH=CH | H | H | $CF_3$ | $CF_3$ |
| CH | Me | H | H | $CF_3$ | $CH=CHCF_3$ |
| CH | Me | H | H | $CF_3$ | $OCHF_2$ |
| CH | Et | H | H | $CF_3$ | $OCHF_2$ |
| CH | $MeOCH_2$ | H | H | $CF_3$ | $CF_3$ |
| CH | $Me_2N$ | H | H | $CF_3$ | $CF_3$ |
| CH | MeNH | H | H | $CF_3$ | $CF_3$ |
| CH | Me | H | H | OMe | $CF_3$ |
| CH | Me | H | H | $CF_3$ | $SCHF_2$ |
| CH | Me | H | H | $CF_3$ | $SO_2CHF_2$ |
| CH | MeO | H | H | $CF_3$ | $CF_3$ |
| CH | MeS | H | H | $CF_3$ | $CF_3$ |
| N | Me | H | H | $CF_3$ | $CF_3$ |
| N | Et | H | H | $CF_3$ | $CF_3$ |
| N | Me | H | H | $CF_3$ | $OCHF_2$ |
| N | Et | H | H | $CF_3$ | $OCHF_2$ |
| N | Me | H | H | $OCF_3$ | $CF_3$ |
| N | Me | H | H | $OCHF_2$ | $CF_3$ |
| N | Me | H | H | CN | $CF_3$ |
| N | Et | H | H | CN | $CF_3$ |
| N | Me | H | H | $OCF_3$ | $OCHF_2$ |
| N | Me | H | H | $CF_3$ | OMe |
| N | Me | H | H | $SCF_3$ | $CF_3$ |

TABLE VI

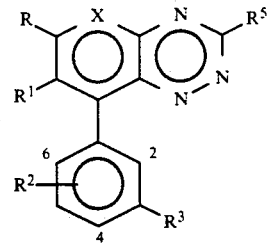

If

| X | R | R¹ | R² | R³ | R⁵ |
|---|---|---|---|---|---|
| CH | Me | H | H | $CF_3$ | $CF_3$ |
| CH | Et | H | H | $CF_3$ | $CF_3$ |
| CH | n-Pr | H | H | $CF_3$ | $CF_3$ |
| CH | Me | H | H | $OCF_3$ | $CF_3$ |
| CH | Et | H | H | $OCF_3$ | $CF_3$ |
| CH | n-Pr | H | H | $OCF_3$ | $CF_3$ |
| CH | Me | H | H | $OCHF_2$ | $CF_3$ |
| CH | Me | H | H | $OCF_3$ | $OCHF_2$ |
| CH | Me | H | H | $CF_3$ | $OCHF_2$ |
| CH | Me | F | H | $CF_3$ | $CF_3$ |
| CH | Me | H | 6-F | $CF_3$ | $CF_3$ |
| CH | Me | H | 4-F | $CF_3$ | $CF_3$ |
| CH | Me | H | 2-OMe | $CF_3$ | $CF_3$ |
| CH | Me | H | 2-$CF_3$ | H | $CF_3$ |
| CH | Me | H | H | Cl | $CF_3$ |
| CH | Et | H | H | $CF_3$ | $OCHF_2$ |
| CH | Me | H | H | Br | $CF_3$ |
| CH | Me | H | H | CN | $CF_3$ |
| CH | Et | H | H | CN | $CF_3$ |
| CH | Me | H | H | $SCF_3$ | $CF_3$ |
| CH | Me | H | H | H | $CF_3$ |
| CH | Me | H | H | $CF_3$ | $OCH_2CF_3$ |
| CH | Me | H | H | $CF_3$ | $SCF_3$ |
| CH | Me | H | H | $CF_3$ | OMe |
| CH | Et | H | H | $CF_3$ | OEt |
| CH | Me | H | H | $CF_3$ | $OCHMe_2$ |
| CH | Me | H | H | $CF_3$ | SMe |
| CH | Me | H | H | $CF_3$ | $CHF_2$ |
| CH | Et | H | H | $CF_3$ | $CHF_2$ |
| CH | Me | H | H | $OCF_3$ | $CHF_2$ |
| CH | Me | H | H | $CF_3$ | $OCF_2CHF_2$ |
| CH | Me | H | H | $CF_3$ | Cl |
| CH | MeCH=CH | H | H | $CF_3$ | $CF_3$ |
| CH | Me | H | H | $CF_3$ | $CH=CHCF_3$ |
| CH | Me | H | H | $CF_3$ | $OCHF_2$ |
| CH | Et | H | H | $CF_3$ | $OCHF_2$ |
| CH | $MeOCH_2$ | H | H | $CF_3$ | $CF_3$ |
| CH | $Me_2N$ | H | H | $CF_3$ | $CF_3$ |
| CH | MeNH | H | H | $CF_3$ | $CF_3$ |
| CH | Me | H | H | OMe | $CF_3$ |
| CH | Me | H | H | $CF_3$ | $SCHF_2$ |
| CH | Me | H | H | $CF_3$ | $SO_2CHF_2$ |
| CH | MeO | H | H | $CF_3$ | $CF_3$ |
| CH | MeS | H | H | $CF_3$ | $CF_3$ |
| N | Me | H | H | $CF_3$ | $CF_3$ |
| N | Et | H | H | $CF_3$ | $CF_3$ |
| N | Me | H | H | $CF_3$ | $OCHF_2$ |
| N | Et | H | H | $CF_3$ | $OCHF_2$ |
| N | Me | H | H | $OCF_3$ | $CF_3$ |
| N | Me | H | H | $OCHF_2$ | $CF_3$ |
| N | Me | H | H | CN | $CF_3$ |
| N | Et | H | H | CN | $CF_3$ |
| N | Me | H | H | $OCF_3$ | $OCHF_2$ |
| N | Me | H | H | $CF_3$ | OMe |
| N | Me | H | H | $SCF_3$ | $CF_3$ |

TABLE VII

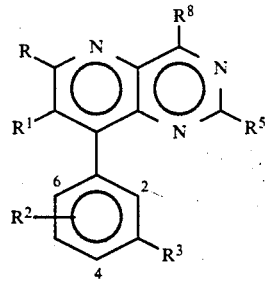

Ig

| X | R | R¹ | R² | R³ | R⁵ | R⁸ |
|---|---|---|---|---|---|---|
| CH | Me | H | H | CF₃ | CF₃ | H |
| CH | Et | H | H | CF₃ | CF₃ | H |
| CH | n-Pr | H | H | CF₃ | CF₃ | H |
| CH | Me | H | H | OCF₃ | CF₃ | H |
| CH | Et | H | H | OCF₃ | CF₃ | H |
| CH | n-Pr | H | H | OCF₃ | CF₃ | H |
| CH | Me | H | H | OCHF₂ | CF₃ | H |
| CH | Me | H | H | OCF₃ | OCHF₂ | H |
| CH | Me | H | H | CF₃ | OCHF₂ | H |
| CH | Me | F | H | CF₃ | CF₃ | H |
| CH | Me | H | 6-F | CF₃ | CF₃ | H |
| CH | Me | H | 4-F | CF₃ | CF₃ | H |
| CH | Me | H | 2-OMe | CF₃ | CF₃ | H |
| CH | Me | H | 2-CF₃ | H | CF₃ | H |
| CH | Me | H | H | Cl | CF₃ | H |
| CH | Et | H | H | CF₃ | OCHF₂ | H |
| CH | Me | H | H | Br | CF₃ | H |
| CH | Me | H | H | CN | CF₃ | H |
| CH | Et | H | H | CN | CF₃ | H |
| CH | Me | H | H | SCF₃ | CF₃ | H |
| CH | Me | H | H | H | CF₃ | H |
| CH | Me | H | H | CF₃ | OCH₂CF₃ | H |
| CH | Me | H | H | CF₃ | SCF₃ | H |
| CH | Me | H | H | CF₃ | OMe | H |
| CH | Et | H | H | CF₃ | OEt | H |
| CH | Me | H | H | CF₃ | OCHMe₂ | H |
| CH | Me | H | H | CF₃ | SMe | H |
| CH | Me | H | H | CF₃ | CHF₂ | H |
| CH | Et | H | H | CF₃ | CHF₂ | H |
| CH | Me | H | H | OCF₃ | CHF₂ | H |
| CH | Me | H | H | CF₃ | OCF₂CHF₂ | H |
| CH | Me | H | H | CF₃ | Cl | H |
| CH | MeCH=CH | H | H | CF₃ | CF₃ | H |
| CH | Me | H | H | CF₃ | CH=CHCF₃ | H |
| CH | Me | H | H | CF₃ | OCHF₂ | H |
| CH | Et | H | H | CF₃ | OCHF₂ | H |
| CH | MeOCH₂ | H | H | CF₃ | CF₃ | H |
| CH | Me₂N | H | H | CF₃ | CF₃ | H |
| CH | MeNH | H | H | CF₃ | CF₃ | H |
| CH | Me | H | H | OMe | CF₃ | H |
| CH | Me | H | H | CF₃ | SCHF₂ | H |
| CH | Me | H | H | CF₃ | SO₂CHF₂ | H |
| CH | MeO | H | H | CF₃ | CF₃ | H |
| CH | MeS | H | H | CF₃ | CF₃ | H |
| CH | Me | H | H | CF₃ | CF₃ | Me |
| CH | Me | H | H | CF₃ | CF₃ | CN |
| CH | Me | H | H | CF₃ | CF₃ | OMe |
| CH | Me | H | H | CF₃ | CF₃ | Cl |
| N | Me | H | H | CF₃ | CF₃ | H |
| N | Et | H | H | CF₃ | CF₃ | H |
| N | Me | H | H | CF₃ | OCHF₂ | H |
| N | Et | H | H | CF₃ | OCHF₂ | H |
| N | Me | H | H | OCF₃ | CF₃ | H |
| N | Me | H | H | OCHF₂ | CF₃ | H |
| N | Me | H | H | CN | CF₃ | H |
| N | Et | H | H | CN | CF₃ | H |
| N | Me | H | H | OCF₃ | OCHF₂ | H |
| N | Me | H | H | CF₃ | OMe | H |
| N | Me | H | H | SCF₃ | CF₃ | H |

TABLE VIII

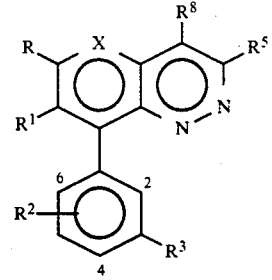

Ih

| X | R | R¹ | R² | R³ | R⁵ | R⁸ |
|---|---|---|---|---|---|---|
| CH | Me | H | H | CF₃ | CF₃ | H |
| CH | Et | H | H | CF₃ | CF₃ | H |
| CH | n-Pr | H | H | CF₃ | CF₃ | H |
| CH | Me | H | H | OCF₃ | CF₃ | H |
| CH | Et | H | H | OCF₃ | CF₃ | H |
| CH | n-Pr | H | H | OCF₃ | CF₃ | H |
| CH | Me | H | H | OCHF₂ | CF₃ | H |
| CH | Me | H | H | OCF₃ | OCHF₂ | H |
| CH | Me | H | H | CF₃ | OCHF₂ | H |
| CH | Me | F | H | CF₃ | CF₃ | H |
| CH | Me | H | 6-F | CF₃ | CF₃ | H |
| CH | Me | H | 4-F | CF₃ | CF₃ | H |
| CH | Me | H | 2-OMe | CF₃ | CF₃ | H |
| CH | Me | H | 2-CF₃ | H | CF₃ | h |
| CH | Me | H | H | Cl | CF₃ | H |
| CH | Et | H | H | CF₃ | OCHF₂ | H |
| CH | Me | H | H | Br | CF₃ | H |
| CH | Me | H | H | CN | CF₃ | H |
| CH | Et | H | H | CN | CF₃ | H |
| CH | Me | H | H | SCF₃ | CF₃ | H |
| CH | Me | H | H | H | CF₃ | H |
| CH | Me | H | H | CF₃ | OCH₂CF₃ | H |
| CH | Me | H | H | CF₃ | SCF₃ | H |
| CH | Me | H | H | CF₃ | OMe | H |
| CH | Et | H | H | CF₃ | OEt | H |
| CH | Me | H | H | CF₃ | OCHMe₂ | H |
| CH | Me | H | H | CF₃ | SMe | H |
| CH | Me | H | H | CF₃ | CHF₂ | H |
| CH | Et | H | H | CF₃ | CHF₂ | H |
| CH | Me | H | H | OCF₃ | CHF₂ | H |
| CH | Me | H | H | CF₃ | OCF₂CHF₂ | H |
| CH | Me | H | H | CF₃ | Cl | H |
| CH | MeCH=CH | H | H | CF₃ | CF₃ | H |
| CH | Me | H | H | CF₃ | CH=CHCF₃ | H |
| CH | Me | H | H | CF₃ | OCHF₂ | H |
| CH | Et | H | H | CF₃ | OCHF₂ | H |
| CH | MeOCH₂ | H | H | CF₃ | CF₃ | H |
| CH | Me₂N | H | H | CF₃ | CF₃ | H |
| CH | MeNH | H | H | CF₃ | CF₃ | H |
| CH | Me | H | H | OMe | CF₃ | H |
| CH | Me | H | H | CF₃ | SCHF₂ | H |
| CH | Me | H | H | CF₃ | SO₂CHF₂ | H |
| CH | MeO | H | H | CF₃ | CF₃ | H |
| CH | MeS | H | H | CF₃ | CF₃ | H |
| CH | Me | H | H | CF₃ | CF₃ | Me |
| CH | Me | H | H | CF₃ | CF₃ | CN |
| CH | Me | H | H | CF₃ | CF₃ | OMe |
| CH | Me | H | H | CF₃ | CF₃ | Cl |
| N | Me | H | H | CF₃ | CF₃ | H |
| N | Et | H | H | CF₃ | CF₃ | H |
| N | Me | H | H | CF₃ | OCHF₂ | H |
| N | Et | H | H | CF₃ | OCHF₂ | H |
| N | Me | H | H | OCF₃ | CF₃ | H |
| N | Me | H | H | OCHF₂ | CF₃ | H |
| N | Me | H | H | CN | CF₃ | H |
| N | Et | H | H | CN | CF₃ | H |
| N | Me | H | H | OCF₃ | OCHF₂ | H |
| N | Me | H | H | CF₃ | OMe | H |
| N | Me | H | H | SCF₃ | CF₃ | H |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid diluent(s). More specifically, they will contain these ingredients in the following approximate proportions:

|  | Active Ingredient | Weight Percent* | |
| --- | --- | --- | --- |
|  |  | Diluent(s) | Surfactant(s) |
| Wettable Powders | 20-90 | 0-74 | 1-10 |
| Oil Suspensions, Emulsions, Solutions, (including Emulsifiable Concentrates) | 3-50 | 40-95 | 0-15 |
| Aqueous Suspension | 10-50 | 40-84 | 1-20 |
| Dusts | 1-25 | 70-99 | 0-5 |
| Granules and Pellets | 0.1-95 | 5-99.9 | 0-15 |
| High Strength Compositions | 90-99 | 0-10 | 0-2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, N.Y., 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., N.Y., 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff. and "Perry's Chemical Engineer's Handbook", 5th Ed., McGraw-Hill, New York, 1973, pp. 8-57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138-140, 162-164, 166, 167 and 169-182;

H. Gysin and E. Knusli, U.S. Pat. No. 2,891,855, Jun. 23, 1959, Col. 3, line 66 through Col. 5, line 17 and Examples 1-4;

G. C. Klingman, "Weed Control as a Science", John Wiley and Sons, Inc., New York, 1961, pp. 81-96; and J. D. Fryer and S. A. Evans, "Weed Control Handbook", 5th Ed., Blackwell Scientific Publications, Oxford, 1968, pp. 101-103.

In the following examples, all parts are by weight unless otherwise indicated.

EXAMPLE A

| Wettable Powder | |
| --- | --- |
| α-(difluoromethoxy)-6-methyl-8-[3-(trifluoromethyl)-phenyl]quinoxaline | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

EXAMPLE B

| Wettable Powder | |
| --- | --- |
| α-(difluoromethoxy)-6-methyl-8-[3-(trifluoromethyl)-phenyl]quinoxaline | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE C

| Granule | |
| --- | --- |
| Wettable Powder of Example B | 5% |
| attapulgite granules (U.S.S. 20-40 mesh; 0.84-0.42 mm) | 95% |

A slurry of wettable powder containing solids is sprayed on the surface of attapulgite granules in a double-cone blender. The granules are dried and packaged.

EXAMPLE D

| Extruded Pellet | |
| --- | --- |
| α-(difluoromethoxy)-6-methyl-8-[3-(trifluoromethyl)-phenyl]quinoxaline | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE E

| Low Strength Granule | |
|---|---|
| α-(difluoromethoxy)-6-methyl-8-[3-(trifluoromethyl)-phenyl]quinoxaline | 1% |
| N,N-dimethylformamide | 9% |
| attapulgite granules (U.S.S. 20 to 40 sieve) | 90% |

The active ingredient is dissolved in the solvent and the solution is sprayed upon dedusted granules in a double-cone blender. After spraying of the solution has been completed, the blender is allowed to run for a short period and then the granules are packaged.

EXAMPLE F

| Granule | |
|---|---|
| α-(difluoromethoxy)-6-methyl-8-[3-(trifluoromethyl)-phenyl]quinoxaline | 80% |
| wetting agent | 1% |
| crude ligninsulfonate salt (containing 5-20 of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14-100 mesh (1410-149 microns), and packaged for use.

EXAMPLE G

| Aqueous Suspension | |
|---|---|
| α-(difluoromethoxy)-6-methyl-8-[3-(trifluoromethyl)-phenyl]quinoxaline | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE H

| High Strength Concentrate | |
|---|---|
| α-(difluoromethoxy)-6-methyl-8-[3-(trifluoromethyl)-phenyl]quinoxaline | 99% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

EXAMPLE I

| Wettable Powder | |
|---|---|
| α-(difluoromethoxy)-6-methyl-8-[3-(trifluoromethyl)-phenyl]quinoxaline | 90% |
| dioctyl sodium sulfosuccinate | 0.1% |
| synthetic fine silica | 9.9% |

The ingredients are blended and ground in a hammer-mill to produce particles essentially all below 100 microns. The material is sifted through a U.S.S. No. 50 screen and then packaged.

EXAMPLE J

| Wettable Powder | |
|---|---|
| α-(difluoromethoxy)-6-methyl-8-[3-(trifluoromethyl)-phenyl]quinoxaline | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE K

| Oil Suspension | |
|---|---|
| α-(difluoromethoxy)-6-methyl-8-[3-(trifluoromethyl)-phenyl]quinoxaline | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

EXAMPLE L

| Dust | |
|---|---|
| α-(difluoromethoxy)-6-methyl-8-[3-(trifluoromethyl)-phenyl]quinoxaline | 10% |
| attapulgite | 10% |
| Pyrophyllite | 80% |

The active ingredient is blended with attapulgite and then passed through a hammer-mill to produce particles substantially all below 200 microns. The ground concentrate is then blended with powdered pyrophyllite until homogeneous.

EXAMPLE M

| Oil Suspension | |
|---|---|
| α-(difluoromethoxy)-6-methyl-8-[3-(trifluoromethyl)-phenyl]quinoxaline | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

UTILITY

Test results indicate compounds of this invention are active postemergence and preemergence herbicides. Many compounds in this invention are useful for the control of selected grass and broadleaf weeds with tolerance to important agronomic crops such as barley (*Hordeum vulgare*), corn (*Zea mays*), cotton (*Gossypium hirsutum*), rice (*Oryza sativa*), sorghum (*Sorghum bicolor*), soybean (*Glycine max*) and wheat (*Triticum aestivum*). Grass and broadleaf weed species controlled include, but are not limited to, barnyardgrass (*Echinochloa crusgalli*), bedstraw (*Galium aparine*), blackgrass (*Alopecurus myosuroides*), cheatgrass (*Bromus secalinus*), chickweed (*Stellaria media*), crabgrass (*Digitaria spp.*), foxtail (*Setaria spp.*), lambsquarters (*Chenopodium spp.*), velvetleaf (*Afutilon theophrasti*), wild buckwheat (*Polygonum convolvulus*) and wild oats (*Avena fatua*).

These compounds also have utility for weed control of selected vegetation in specified areas such as around storage tanks, parking lots, highways, and railways; in fallow crop areas; and in citrus and plantation crops such as banana, coffee, oil palm, and rubber.

Rates of application for compounds of this invention are determined by a number of factors. These factors include: formulation selected, method of application, amount and type of vegetation present, growing conditions, etc. In general terms, the subject compounds should be applied at rates from 0.01 to 20 kg/ha with a preferred rate range of 0.02 to 2 kg/ha. Although a small number of compounds show slight herbicidal activity at the rates tested, it is anticipated these compounds are herbicidally active at higher application rates. One skilled in the art can easily determine application rates necessary for desired level of weed control.

Compounds of this invention may be used alone or in combination with other commercial herbicides, insecticides, or fungicides. The following list exemplifies some of the herbicides suitable for use in mixtures. A combination of a compound from this invention with one or more of the following herbicides may be particularly useful for weed control.

| Common Name | Chemical Name |
|---|---|
| acetochlor | 2-chloro-N-(ethoxymethyl)-N-(2-ethyl-6-methylphenyl)-acetamide |
| acifluorfen | 5-[2-chloro-4-(trifluoromethyl)-phenoxy]-2-nitrobenzoic acid |
| aclonifen | 2-chloro-6-nitro-3-phenoxybenzenamine |
| acrolein | 2-propenal |
| alachlor | 2-chloro-N-(2,6-diethylphenyl)-N-(methoxymethyl)acetamide |
| alloxydim | methyl 2,2-dimethyl-4,6-dioxo-5-[1-[(2-propenyloxy)amino]-butylidene]cyclohexanecarboxylate |
| ametryn | N-ethyl-N'-(1-methylethyl)-6-(methylthio)-1,3,5-triazine-2,4-diamine |
| amitrole | 1H-1,2,4-triazol-3-amine |
| AMS | ammonium sulfamate |
| anilofos | S-[2-[(4-chlorophenyl)(1-methylethyl)amino]-2-oxoethyl] O,O-dimethylphosphorodithioate |
| asulam | methyl [(4-aminophenyl)sulfonyl]-carbamate |
| atrazine | 6-chloro-N-ethyl-N'-(1-methylethyl)-1,3,5-triazine-2,4-diamine |
| aziprotryne | 4-azido-N-(1-methylethyl)-6-methylthio-1,3,5-triazin-2-amine |
| azoluron | N-(1-ethyl-1H-pyrazol-5-yl)-N'-phenylurea |
| barban | 4-chloro-2-butynyl 3-chlorocarbamate |
| benazolin | 4-chloro-2-oxo-3(2H)-benzothiazole acetic acid |
| benfluralin | N-butyl-N-ethyl-2,6-dinitro-4-(trifluoromethyl)benzenamine |
| bensulfuron | 2-[[[[[(4,6-dimethoxy-2-pyrimidinyl)amino]methylcarbonyl]-amino]sulfonyl]methyl]benzoic acid, methyl ester |
| bensulide | O,O-bis(1-methylethyl) S-[2-[(phenylsulfonyl)amino]ethyl]-phosphorodithioate |
| bentazon | 3-(1-methylethyl)-(1H)-2,1,3-benzothiadiazin-4(3H)-one, 2,2-dioxide |
| benzofluor | N-[4-(ethylthio)-2-(trifluoromethyl)phenyl]methanesulfonamide |
| benzoylprop | N-benzoyl-N-(3,4-dichlorophenyl)-DL-alanine |
| benzthiazuron | N-2-benzothiazolyl-N'-methylurea |
| bialaphos | 4-(hydroxymethylphosphinyl)-L-2-aminobutanoyl-L-alanyl-L-alanine |
| bifenox | methyl 5-(2,4-dichlorophenoxy)-2-nitrobenzoate |
| bromacil | 5-bromo-6-methyl-3-(1-methylpropyl)-2,4(1H,3H)pyrimidine-dione |
| *bromobutide | (+)2-bromo-3,3-dimethyl-N-(1-methyl-1-phenylethyl)butanamide |
| bromofenoxim | 3,5-dibromo-4-hydroxybenzaldhyde O-(2,4-dinitrophenyl)oxime |
| bromoxynil | 3,5-dibromo-4-hydroxybenzonitrile |
| bromuron | N'-(4-bromophenyl)-N,N-dimethylurea |
| buminafos | dibutyl [1-(butylamino)cyclohexyl]phosphonate |
| butachlor | N-(butoxymethyl)-2-chloro-N-(2,6-diethylphenyl)acetamide |
| butamifos | O-ethyl O-(5-methyl-2-nitrophenyl)(1methylpropyl)phosphoramidothioate |
| buthidazole | 3-[5-(1,1-dimethylethyl)-1,3,4-thiadiazol-2-yl]-4-hydroxy-1-methyl-2-imidazolidinone |
| butralin | 4-(1,1-dimethylethyl)-N-(1-methylpropyl)-2,6-dinitrobenzenamine |
| butylate | S-ethyl bis(2-methylpropyl)-carbamothioate |
| cacodylic acid | dimethyl arsinic oxide |
| carbetamide | (R)-N-ethyl-2-[[(phenylamino)-carbonyl]oxy]propanamide |
| CDAA | 2-chloro-N,N-di-2-propenylacetamide |
| CDEC | 2-chloroallyl diethyldithiocarbamate |
| chlomethoxyfen | 4-(2,4-dichlorophenoxy)-2-methoxy-1-nitrobenzene |
| chloramben | 3-amino-2,5-dichlorobenzoic acid |

| Common Name | Chemical Name |
|---|---|
| chlorbromuron | 3-(4-bromo-3-chlorophenyl)-1-methoxy-1-methylurea |
| chlorbufam | 1-methyl-2-propynl(3-chlorophenyl)carbamate |
| chlorfenac | 2,3,6-trichlorobenzeneacetic acid |
| chlorflurecol-methyl | methyl 2-chloro-9-hydroxy-9H-fluorene-9-carboxylate |
| chloridazon | 5-amino-4-chloro-2-phenyl-3(2H)-pyridazinone |
| chlorimuron | 2-[[[[(4-chloro-6-methoxy-2-pyrimidinyl)ethylamino]carbonyl]amino]sulfonyl]-benzoic acid, ethyl ester |
| chlornitrofen | 1,3,5-trichloro-2-(4-nitrophenoxy)benzene |
| chloropicrin | trichloronitromethane |
| chloroxuron | N'-[4-(4-chlorophenoxy)phenyl]-N,N-dimethylurea |
| chlorpropham | 1-methylethyl 3-chlorophenylcarbamate |
| chlorsulfuron | 2-chloro-N-[[(4-methoxy-6-methyl-1,3,5-triazin-2-yl)-amino]carbonyl] benzenesulfonamide |
| chlorthal-dimethyl | dimethyl 2,3,5,6-tetrachloro-1,4-benzenedicarboxylate |
| chlorthiamid | 2,6-dichlorobenzene carbothioamide |
| chlortoluron | N'-(3-chloro-4-methylphenyl)-N,N-dimethylurea |
| cinmethylin | exo-1-methyl-4-(1-methylethyl)-2-[(2-methylphenyl)methoxy]-7-oxabicyclo[2.2.1]heptane |
| clethodim | (E,E)-(+)-2-[1-[[(3-chloro-2-propenyl)oxy]imino]propyl]-5-[2-(ethylthio)propyl]-3-hydroxy-2-cyclohexen-1-one |
| clomazone | 2-[(2-chlorophenyl)methyl]-4,4-dimethyl-3-isoxazolidinone |
| cloproxydim | (E,E)-2-[1-[[(3-chloro-2-propenyl)oxy]imino]butyl]]-5-[2-(ethylthio)propyl]-3-hydroxy-2-cyclohexen-1-one |
| clopyralid | 3,6-dichloro-2-pyridinecarboxylic acid |
| CMA | calcium salt of MAA |
| cyanazine | 2-[[4-chloro-6-(ethylamino)-1,3,5-triazin-2-yl]amino]-2-methylpropanenitrile |
| cycloate | S-ethyl cyclohexylethylcarbamothioate |
| cycloxydim | 2-[1-ethoxyimino)butyl]-3-hydroxy-5-(tetrahydro-2H-thiopyran-3-yl)-2-cyclohexene-1-one |
| cycluron | 3-cyclooctyl-1,1-dimethylurea |
| cyperquat | 1-methyl-4-phenylpyridinium |
| cyprazine | 2-chloro-4-(cyclopropylamino)-6-(isopropylamino)-s-triazine |
| cyprazole | N-[5-(2-chloro-1,1-dimethylethyl)-1,3,4-thiadiazol-2-yl]cyclopropanecarboxamide |
| cypromid | 3',4'-dichlorocyclopropanecarboxanilide |
| dalapon | 2,2-dichloropropanoic acid |
| dazomet | tetrahydro-3,5-dimethyl-2H-1,3,5-thiadiazine-2-thione |
| DCPA | dimethyl 2,3,5,6-tetrachloro-1,4-benzenedicarboxylate |
| desmedipham | ethyl [3-[[(phenylamino)carbonyl]oxy]phenyl]carbamate |
| desmetryn | 2-(isopropylamino)-4-(methylamino)-6-(methylthio)-s-triazine |
| diallate | S-(2,3-dichloro-2-propenyl)bis(1-methylethyl)carbamothioate |
| dicamba | 3,6-dichloro-2-methoxybenzoic acid |
| dichlobenil | 2,6-dichlorobenzonitrile |
| dichlorprop | (+)-2-(2,4-dichlorophenoxy)propanoic acid |
| *diclofop-methyl | (+)-2-[4-(2,4-dichlorophenoxy)-phenoxy]propanoic acid, methyl ester |
| diethatyl | N-(chloroacetyl)-N-(2,6-diethylphenyl)glycine |
| difenoxuron | N'-[4-(4-methoxyphenoxy)phenyl]-N,N-dimethylurea |
| difenzoquat | 1,2-dimethyl-3,5-diphenyl-1H-pyrazolium ion |
| diflufenican | N-(2,4-difluorophenyl)-2-(3-trifluoromethylphenoxy)pyridine-3-carboxamide |
| dimefuron | N'-[3-chloro-4-[5-(1,1-dimethylethyl)-2-oxo-1,3,4-oxadiazol-3(2H)-yl]phenyl]-N,N-dimethylurea |
| dimethachlor | 2-chloro-N-(2,6-dimethylphenyl)-N-(2-methoxyethyl)acetamide |
| dimethametryn | N-(1,2-dimethylpropyl)-N'-ethyl-6-(methylthio)-1,3,5-triazine-2,4-diamine |
| dimethipin | 2,3-dihydro-5,6-dimethyl-1,4-dithiin 1,1,4,4-tetraoxide |
| dimethylarsinic | dimethylarsinic acid |
| dinitramine | N3,N3-diethyl-2,4-dinitro-6-(trifluoromethyl)-1,3-benzenediamine |
| dinoseb | 2-(1-methylpropyl)-4,6-dinitrophenol |
| dinoterb | 2-(1,1-dimethylethyl)-4,6-dinitrophenol |
| diphenamid | N,N-dimethyl-a-phenylbenzeneacetamide |
| dipropetryn | 6-(ethylthio)-N,N'-bis(1-methylethyl)-1,3,5-triazine-2,4-diamine |
| diquat | 6,7-dihydrodipyrido[1,2-a:2',1'-c]pyrazinediium ion |
| diuron | N'-(3,4-dichlorophenyl)-N,N-dimethylurea |
| DNOC | 2-methyl-4,6-dinitrophenol |
| DPX-V9360 | 2-[[(4,6-dimethoxypyrimidin-2-yl)aminocarbonyl]aminosulfonyl]-N,N-dimethyl-3-pyridinecarboxamide |
| DSMA | disodium salt of MAA |
| dymron | N-(4-methylphenyl)-N'-(1-methyl-1-phenylethyl)urea |
| eglinazine-ethyl | N-[4-chloro-6-(ethylamino)-1,3,5-triazin-2-yl]glycine ethyl ester |
| endothall | 7-oxabicyclo[2.2.1]heptane-2,3-dicarboxylic acid |
| EPTC | S-ethyl dipropylcarbamothioate |
| ethalfluralin | N-ethyl-N-(2-methyl-2-propenyl)-2,6-dinitro-4-(trifluoromethyl)-benzenamine |
| ethidimuron | N-[5-(ethylsulfonyl)-1,3,4-thiadiazol-2-yl]-N,N'-dimethylurea |
| *ethofumesate | (+)-2-ethoxy-2,3-dihydro-3,3-dimethyl-5-benzofuranyl methanesulfonate |
| fenac | 2,3,6-trichlorobenzeneacetic acid |
| *fenoprop | (+)-2-(2,4,5-trichlorophenoxy)-propanoic acid |
| *fenoxaprop | (+)-2-[4-[(6-chloro-2-benzoxazolyl)oxy]phenoxy]propanoic acid |
| fenuron | N,N-dimethyl-N'-phenylurea |
| fenuron TCA | Salt of fenuron and TCA |
| flamprop-M-isopropyl | 1-methylethyl N-benzoyl-N-(3-chloro-4-fluorophenyl)-D-alanine |
| flamprop-methyl | methyl N-benzoyl-N-(3-chloro-4-fluorophenyl)-DL-alaninate |
| *fluazifop | (+)-2-[4-[[5-(trifluoromethyl)-2-pyridinyl]oxy]phenoxy]propanoic acid |
| fluazifop-P | (R)-2-[4-[[5-(trifluoromethyl)-2-pyridinyl]oxy]phenoxy]propanoic acid |
| fluchloralin | N-(2-chloroethyl)-2,6-dinitro-N-propyl-4-(trifluoromethyl)-benzenamine |
| fluometuron | N,N-dimethyl-N'-[3-(trifluoro- |

-continued

| Common Name | Chemical Name |
|---|---|
| fluralin | N-butyl-N-ethyl-2,6-dinitro-4-(trifluoromethyl)benzenamine |
| fluorodifen | p-nitrophenyl a,a,a-trifluoro-2-nitro-p-tolyl ether |
| fluoroglycofen | carboxymethyl 5-[2-chloro-4-(trifluoromethyl)phenoxy]-2-nitrobenzoate |
| flurecol-butyl | butyl 9-hydroxy-9H-fluorene-9-carboxylate |
| fluridone | 1-methyl-3-phenyl-5-[3-(trifluoromethyl)phenyl]-4(1H)-pyridinone |
| flurochloridone | 3-chloro-4-(chloromethyl)-1-[3-(trifluoromethyl)phenyl]-2-pyrrolidinone |
| fluroxypyr | [(4-amino-3,5-dichloro-6-fluoro-2-pyridinyl)oxy]acetic acid |
| fomesafen | 5-[2-chloro-4-(trifluoromethyl)-phenoxy]-N-(methylsulfonyl)-2-nitrobenzamide |
| fosamine-ammonium | ethyl hydrogen (aminocarbonyl)phosphonate ammonium ethyl |
| glufosinate-ammonium | ammonium 2-amino-4-(hydroxymethylphosphinyl)butanoate |
| glyphosate | N-(phosphonomethyl)glycine |
| haloxyfop | 2-[4-[[3-chloro-5-(trifluoromethyl)-2-pyridinyl]oxy]-phenoxy]propanoic acid |
| hexaflurate | potassium hexafluoroarsenate |
| hexazinone | 3-cyclohexyl-6-(dimethylamino)-1-methyl-1,3,5-triazine-2,4(1H,3H)dione |
| imazamethabenz | 6-(4-isopropyl-4-methyl-5-oxo-2-imidazolin-2-yl)-m-toluic acid, methyl ester and 6-(4-isopropyl-4-methyl-5-oxo-2-imidazolin-2-yl)-p-toluic acid, methyl ester |
| imazapyr | (+)-2-[4,5-dihydro-4-methyl-4-(1-methylethyl)-5-oxo-1H-imidazol-2-yl]-3-pyridinecarboxylic acid |
| imazaquin | 2-[4,5-dihydro-4-methyl-4-(1-methylethyl)-5-oxo-1H-imidazol-2-yl]-3-quinolinecarboxylic acid |
| imazethapyr | (+)-2-[4,5-dihydro-4-methyl-4-(1-methylethyl)-5-oxo-1H-imidazol-2-yl]-5-ethyl-3-pyridine carboxylic acid |
| ioxynil | 4-hydroxy-3,5-diiodobenzonitrile |
| isocarbamid | N-(2-methylpropyl)-2-oxo-1-imidazolidinecarboxamide |
| isopropalin | 4-(1-methylethyl)-2,6-dinitro-N,N-dipropylbenzenamine |
| isoproturon | N-(4-isopropylphenyl)-N',N'-dimethylurea |
| isouron | N'-[5-(1,1-dimethylethyl)-3-isoxazolyl]-N,N-dimethylurea |
| isoxaben | N-[3-(1-ethyl-1-methylpropyl)-5-isoxazolyl]-2,6-dimethoxybenzamide |
| karbutilate | 3-[[(dimethylamino)carbonyl]-amino]phenyl-(1,1-dimethylethyl)carbamate |
| lactofen | (+)-2-ethoxy-1-methyl-2-oxoethyl-5-[2-chloro-4-(trifluoromethyl)phenoxy]-2-nitrobenzoate |
| lenacil | 3-cyclohexyl-6,7-dihydro-1H-cyclopentapyrimidine-2,4(3H,5H)-dione |
| linuron | N'-(3,4-dichlorophenyl)-N-methoxy-N-methylurea |
| MAA | methylarsonic acid |
| MAMA | monoammonium salt of MAA |
| MCPA | (4-chloro-2-methylphenoxy)acetic acid |
| MCPA-thioethyl | S-ethyl (4-chloro-2-methylphenoxy)ethanethioate |
| MCPB | 4-(4-chloro-2-methylphenoxy)butanoic acid |
| mecoprop | (+)-2-(4-chloro-2-methylphenoxy)propanoic acid |

-continued

| Common Name | Chemical Name |
|---|---|
| mefenacet | 2-(2-benzothiazolyloxy)-N-methyl-N-phenyl acetamide |
| mefluidide | N-[2,4-dimethyl-5-[[(trifluoromethyl)sulfonyl]amino]phenyl]-acetamide |
| metamitron | 4-amino-3-methyl-6-phenyl-1,2,4-triazin-5(4H)-one |
| metazachlor | 2-chloro-N-(2,6-dimethylphenyl)-N-(1(H)-pyrazol-1-ylmethyl)-acetamide |
| methabenzthiazuron | 1,3-dimethyl-3-(2-benzothiazolyl)-urea |
| methalpropalin | N-(2-methyl-2-propenyl)-2,6-dinitro-N-propyl-4-(trifluoromethyl)benzenamide |
| metham | methylcarbamodithioic acid |
| methazole | 2-(3,4-dichlorophenyl)-4-methyl-1,2,4-oxadiazolidine-3,5-dione |
| methoxuron | N'-(3-chloro-4-methoxyphenyl)-N,N-dimethylurea |
| methoxyphenone | (4-methoxy-3-methylphenyl)(3-methylphenyl)methanone |
| methyldymron | N-methyl-N'-(1-methyl-1-phenylethyl)-N-phenylurea |
| metobromuron | N'-(4-bromophenyl)-N-methoxy-N-methylurea |
| metolachlor | 2-chloro-N-(2-ethyl-6-methylphenyl)-N-(2-methoxy-1-methylethyl)acetamide |
| metoxuron | N'-(3-chloro-4-methoxyphenyl)-N,N-dimethylurea |
| metribuzin | 4-amino-6-(1,1-dimethylethyl)-3-(methylthio)-1,2,4-triazin-5(4H)-one |
| metsulfuron methyl | 2-[[[[(4-methoxy-6-methyl-1,3,5-triazin-2-yl)amino]carbonyl]-amino]sulfonyl]benzoic acid, methyl ester |
| MH | 1,2-dihydro-3,6-pyridazinedione |
| molinate | S-ethyl hexahydro-1H-azepine-1-carbothioate |
| monalide | N-(4-chlorophenyl)-2,2-dimethylpentanamide |
| monolinuron | 3-(p-chlorophenyl)-1-methoxy-1-methylurea |
| monuron | N'-(4-chlorophenyl)-N,N-dimethylurea |
| MSMA | monosodium salt of MAA |
| naproanilide | 2-(2-naphthalenyloxy)-N-phenylpropanamide |
| napropamide | N,N-diethyl-2-(1-naphthalenyloxy)propanamide |
| naptalam | 2-[(1-naphthalenylamino)carbonyl]benzoic acid |
| neburon | 1-butyl-3-(3,4-dichlorophenyl)-1-methylurea |
| nitralin | 4-methylsulfonyl-2,6-dinitro-N,N-dipropylaniline |
| nitrofen | 2,4-dichloro-1-(4-nitrophenoxy)-benzene |
| nitrofluorfen | 2-chloro-1-(4-nitrophenoxy)-4-(trifluoromethyl)benzene |
| norea | N,N-dimethyl-N'-(octahydro-4,7-methano-1H-inden-5-yl)urea-3aa,4a,5a,7a,7aa-isomer |
| norflurazon | 4-chloro-5-(methylamino)-2-[3-(trifluoromethyl)phenyl]-3(2H)-pyridazinone |
| orbencarb | S-[2-(chlorophenyl)methyl]diethylcarbamothioate |
| oryzalin | 4-(dipropylamino)-3,5-dinitrobenzenesulfonamide |
| oxadiazon | 3-[2,4-dichloro-5-(1-methylethoxy)phenyl]-5-(1,1-dimethylethyl)-1,3,4-oxadiazol-2(3H)-one |
| oxyfluorfen | 2-chloro-1-(3-ethoxy-4-nitrophenoxy)-4-(trifluoromethyl)benzene |
| paraquat | 1,1'-dimethyl-4,4'-dipyridinium ion |

-continued

| Common Name | Chemical Name |
|---|---|
| pebulate | S-propyl butylethylcarbamothioate |
| pendimethalin | N-(1-ethylpropyl)-3,4-dimethyl-2,6-dinitrobenzenamine |
| perfluidone | 1,1,1-trifluoro-N-[2-methyl-4-(phenylsulfonyl)phenyl]methanesulfonamide |
| phenisopham | 3-[[(1-methylethoxy)carbonyl]amino]phenyl ethylphenylcarbamate |
| phenmedipham | 3-[(methoxycarbonyl)amino]phenyl (3-methylphenyl)carbamate |
| picloram | 4-amino-3,5,6-trichloro-2-pyridinecarboxylic acid |
| piperophos | S-[2-(2-methyl-1-piperidinyl)-2-oxo-ethyl]O,O-dipropyl phosphorodithioate |
| pretilachlor | 2-chloro-N-(2,6-diethylphenyl)-N-(2-propoxyethyl)acetamide |
| procyazine | 2-[[4-chloro-6-(cyclopropylamino)-1,3,5-triazine-2-yl]amino]-2-methylpropanenitrile |
| prodiamine | 2,4-dinitro-N3,N3-dipropyl-6-(trifluoromethyl)-1,3-benzenediamine |
| profluralin | N-(cyclopropylmethyl)-2,6-dinitro-N-propyl-4-(trifluoromethyl)-benzenamine |
| proglinazine-ethyl | N-[4-chloro-6-[(1-methylethyl)amino]-1,3,5-triazin-2-yl]-glycine ethyl ester |
| prometon | 6-methoxy-N,N'-bis(1-methylethyl)-1,3,5-triazine-2,4-diamine |
| prometryn | N,N'-bis(1-methylethyl)-6-(methylthio)-1,3,5-triazine-2,4-diamine |
| pronamide | 3,5-dichloro-N-(1,1-dimethyl-2-propynyl)benzamide |
| propachlor | 2-chloro-N-(1-methylethyl)-N-phenylacetamide |
| propanil | N-(3,4-dichlorophenyl)propanamide |
| propaquizafop | 2-[[(1-methylethylidene)amino]oxy]ethyl-2-[4-[(6-chloro-2-quinoxalinyl)oxy]phenoxy]-propanoate |
| propazine | 6-chloro-N,N'-bis(1-methylethyl)-1,3,5-triazine-2,4-diamine |
| propham | 1-methylethyl phenylcarbamate |
| propyzamide | 3,5-dichloro-N-(1,1-dimethyl-2-propynl)benzamide |
| prosulfalin | N-[[4-(dipropylamino)-3,5-dinitrophenyl]sulfonyl]-S,S-dimethyl-sulfilimine |
| prosulfocarb | S-benzyldipropylthiocarbamate |
| prynachlor | 2-chloro-N-(1-methyl-2-propynyl)-acetanilide |
| pyrazon | 5-amino-4-chloro-2-phenyl-3(2H)-pyridazinone |
| pyrazosulfuron-ethyl | ethyl 5-[[[[(4,6-dimethoxy-2-pyrimidinyl)amino]carbonyl]-amino]sulfonyl]-1-methyl-1H-pyrazole-4-carboxylate |
| pyrazoxyfen | 2-[[4-(2,4-dichlorobenzoyl)-1,3-dimethyl-1H-pyrazol-5-yl]-oxy]-1-phenylethanone |
| pyridate | O-(6-chloro-3-phenyl-4-pyridazinyl) S-octyl carbonothioate |
| quizalofop ethyl | (+)-2-[4-[(6-chloro-2-quinoxalinyl)oxy]phenoxy]propanoic acid, ester |
| secbumeton | N-ethyl-6-methoxy-N'-(1-methylpropyl)-1,3,5-triazine-2,4-diamine |
| sethoxydim | 2-[1-(ethoxyimino)butyl]-5-[2-(ethylthio)propyl]-3-hydroxy-2-cyclohexen-1-one |
| siduron | N-(2-methylcyclohexyl)-N'-phenylurea |
| simazine | 6-chloro-N,N'-diethyl-1,3,5-triazine-2,4-diamine |
| simetryn | N,N'-diethyl-6-(methylthio)-1,3,5-triazine-2,4-diamine |
| sodium chlorate | sodium chlorate |
| sodium monochloroacetate | chloroacetic acid, sodium salt |
| sulfometuron methyl | 2-[[[[(4,6-dimethyl-2-pyrimidinyl)amino]carbonyl]amino]-sulfonyl]benzoic acid, methyl ester |
| 2,4,5-T | (2,4,5-trichlorophenoxy)acetic acid |
| 2,3,6-TBA | 2,3,6-trichlorobenzoic acid |
| TCA | trichloroacetic acid |
| tebutam | 2,2-dimethyl-N-(1-methylethyl)-N-(phenylmethyl)propanamide |
| tebuthiuron | N-[5-(1,1-dimethylethyl)-1,3,4-thiadiazol-2-yl]-N,N'-dimethyl-urea |
| terbacil | 5-chloro-3-(1,1-dimethylethyl)-6-methyl-2,4(1H,3H)-pyrimidinedione |
| terbuchlor | N-(butoxymethyl)-2-chloro-N-[2-(1,1-dimethylethyl)-6-methyl-phenyl]acetamide |
| terbumeton | N-(1,1-dimethylethyl)-N'-ethyl-6-methoxy-1,3,5-triazine-2,4-diamine |
| terbuthylazine | 2-(tert-butylamino)-4-chloro-6-(ethylamino)-s-triazine |
| terbutol | 2,6-di-tert-butyl-p-tolyl methylcarbamate |
| terbutryn | N-(1,1-dimethylethyl)-N'-ethyl-6-(methylthio)-1,3,5-triazine-2,4-diamine |
| thifensulfuron | 3-[[[[(4-methoxy-6-methyl-1,3,5,triazin-2-yl)amino]-carbonyl]amino]sulfonyl]-2-thiophenecarboxylic acid, methyl ester |
| thiameturon-methyl | methyl 3-[[[[(4-methoxy-6-methyl-1,3,5-triazin-2-yl)-amino]carbonyl]amino]-sulfonyl]2-thiophenecarboxylate |
| thiazafluron | N,N'-dimethyl-N-[5-(trifluoromethyl)-1,3,4-thiadiazol-2-yl]urea |
| thiobencarb | S-[(4-chlorophenyl)methyl]-diethylcarbamothioate |
| tiocarbazil | S-(phenylmethyl) bis(1-methylpropyl)carbamothioate |
| tralkoxydim | 2-[1-(ethoxyimino)propyl]-3-hydroxy-5-(2,4,6-trimethylphenyl)-2-cyclohexen-1-one |
| triallate | S-(2,3,3-trichloro-2-propenyl)-bis(1-methylethyl)carbamothioate |
| triasulfuron | 2-(2-chloroethoxy)-N-[[(4-methoxy-6-methyl-1,3,5-triazin-2-yl)-amino]carbonyl]benzenesulfonamide |
| tribenuron methyl | 2-[[[[N-(4-methoxy-6-methyl-1,3,5-triazine-2-yl)-N-methylamino]-carbonyl]amino]sulfonyl]benzoic acid, methyl ester |
| triclopyr | [(3,5,6-trichloro-2-pyridinyl)-oxy]acetic acid |
| *tridiphane | (+)2-(3,5-dichlorophenyl)-2-(2,2,2-trichloroethyl)oxirane |
| trietazine | 6-chloro-N,N,N'-triethyl-1,3,5-triazine-2,4-diamine |
| trifluralin | 2,6-dinitro-N,N-dipropyl-4-(trifluoromethyl)benzenamine |
| trimeturon | 1-(p-chlorophenyl)-2,3,3-trimethylpseudourea |
| 2,4-D | (2,4-dichlorophenoxy)acetic acid |
| 2,4-DB | 4-(2,4-dichlorophenoxy)butanoic acid |
| vernolate | S-propyl dipropylcarbamothioate |
| xylachlor | 2-chloro-N-(2,3-dimethylphenyl)-N-(1-methylethyl)acetamide |

Selective herbicidal properties of the subject compounds were discovered in greenhouse tests as described below.

tivum), wild buckwheat (*Polygonum convolvulus*), and wild oat (*Avena fatua*) and purple nutsedge (*Cyperus rotundus*) tubers were planted and treated preemergence with test chemicals dissolved in a non-phytotoxic solvent. At the same time, these crop and weed species were also treated with postemergence applications of test chemicals. Plants ranged in height from two to eighteen cm (one to four leaf stage) for postemergence treatments. Treated plants and controls were maintained in a greenhouse for twelve to sixteen days, after which all species were compared to controls and visually evaluated. Plant response ratings, summarized in Table A, are based on a scale of 0 to 10 where 0 is no effect and 10 is complete control. A dash (—) response means no test result.

TABLE OF COMPOUNDS

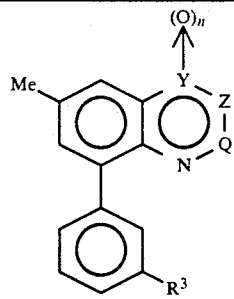

| COMPOUND | $R^3$ | Y | Z | Q | n | m.p. (°C.) |
|---|---|---|---|---|---|---|
| 1 | $CF_3$ | CH | CH | C—$OCH_2CF_3$ | 0 | oil |
| 2 | $CF_3$ | N | C—$OCH_2CF_3$ | CH | 0 | 114–117 |
| 3 | $CF_3$ | N | C—OMe | CH | 0 | 141–142 |
| 4 | $CF_3$ | N | CH | C—OMe | 0 | 119–121 |
| 5 | $CF_3$ | N | N | C—$OCH_2CF_3$ | 1 | 168–169 |
| 6 | $CF_3$ | N | N | C—$OCH_2CF_3$ | 0 | 140–141 |
| 7 | $CF_3$ | N | CH | C—$OCH_2CF_3$ | 0 | 46–48 |
| 8 | $CF_3$ | N | C—$CF_3$ | CH | 0 | 93–94 |
| 9 | $CF_3$ | N | CH | C—$CF_3$ | 0 | 117–118 |
| 10 | $CF_3$ | N | N | C—$OCHF_2$ | 1 | 128–129 |
| 11 | $CF_3$ | N | N | C—$OCHF_2$ | 0 | 109–110 |
| 12 | $CF_3$ | N | N | C—OMe | 1 | 147–148 |
| 13 | $CF_3$ | N | N | C—OMe | 0 | 117–118 |
| 14 | $CF_3$ | N | C—$OCHF_2$ | CH | 0 | 105–106 |
| 15 | $CF_3$ | N | CH | C—$OCHF_2$ | 0 | 103–104 |
| 16 | CN | N | C—$CF_3$ | CH | 0 | 165–166 |
| 17 | CN | N | CH | C—$CF_3$ | 0 | 171–172 |

TEST A

Seeds of barley (*Hordeum vulgare*), barnyardgrass (*Echinochloa crus-galli*), blackgrass (*Alopecurus myosuroides*), cheatgrass (*Bromus secalinus*), chickweed (*Stellaria media*), cocklebur (*Xanthium pensylvanicum*), corn (*Zea mays*), cotton (*Gossypium hirsutum*), crabgrass (*Digitaria spp.*), bedstraw (*Galium aparine*), giant foxtail (*Setaria faberii*), lambsquarters (*Chenopodium album*), morningglory (*Ipomoea hederacea*), rape (*Brassica napus*), rice (*Oryza sativa*), sorghum (*Sorghum bicolor*), soybean (*Glycine max*), sugar beet (*Beta vulcaris*), velvetleaf (*Abutilon theophrasti*), wheat (*Triticum aes-

TABLE A

| | COMPOUND | | | | | | | | | | | | | | | | | | | | |
|---|---|---|---|---|---|---|---|---|---|---|---|---|---|---|---|---|---|---|---|---|---|
| | Rate (2000 g/ha) | | | | Rate (400 g/ha) | | | | | | | | | | | | | | | | |
| | 1 | 3 | 4 | 5 | 1 | 2 | 3 | 4 | 5 | 7 | 8 | 9 | 10 | 11 | 12 | 13 | 14 | 15 | 16 | 17 |
| POST-EMERGENCE | | | | | | | | | | | | | | | | | | | | |
| Barley | 0 | 0 | 2 | 3 | 0 | 0 | 0 | 2 | 0 | 3 | 2 | 3 | 2 | 3 | 4 | 5 | 4 | 2 | 2 | 2 |
| Barnyardgrass | 1 | 1 | 3 | — | 0 | 2 | 1 | 1 | — | 4 | 2 | 5 | 5 | 2 | 3 | 5 | 5 | 9 | 4 | 8 |
| Bedstraw | 5 | 1 | 6 | 5 | 0 | 3 | 1 | 2 | 2 | 7 | 4 | 6 | 7 | 6 | 7 | 6 | 6 | 7 | 3 | 5 |
| Blackgrass | 0 | 0 | 4 | 3 | 0 | 0 | 0 | 2 | 2 | 2 | 3 | 3 | 6 | 5 | 5 | 7 | 4 | 8 | 2 | 3 |
| Cheatgrass | 0 | 0 | 2 | 2 | 0 | 1 | 0 | 1 | 0 | 2 | 0 | 2 | 5 | 4 | 5 | 6 | 2 | 4 | 1 | 2 |
| Chickweed | 4 | 1 | 7 | 5 | 2 | 3 | 0 | 5 | 2 | 4 | 4 | 5 | 7 | 6 | 7 | 7 | 7 | 7 | 4 | 7 |
| Cocklebur | 5 | 2 | 8 | — | 2 | 4 | 2 | 4 | — | — | — | — | — | — | — | 7 | 8 | 3 | — |
| Corn | 0 | 2 | 1 | 2 | 0 | 1 | 0 | 1 | 2 | 1 | 2 | 2 | 3 | 2 | 2 | 2 | 3 | 5 | 2 | 2 |
| Cotton | 8 | 3 | 5 | 3 | 0 | 8 | 0 | 1 | — | 2 | 2 | 3 | 8 | 4 | 5 | 6 | 3 | 9 | 5 | 8 |
| Crabgrass | — | 1 | 2 | 2 | — | 1 | 1 | 2 | 1 | 2 | 3 | 6 | 5 | 4 | 4 | 3 | 4 | 9 | 2 | 7 |
| Giant foxtail | 0 | 2 | 1 | 3 | 0 | 2 | 1 | 2 | 2 | 3 | 2 | 2 | 6 | 3 | 5 | 5 | 4 | 5 | 3 | 5 |
| Lambsquarters | 4 | 6 | 6 | 8 | 3 | 5 | 2 | 4 | 4 | 9 | 3 | 9 | 6 | 7 | 8 | 7 | 10 | 10 | 10 | 10 |
| Morningglory | 2 | 4 | 7 | 8 | 2 | 6 | 4 | 5 | 3 | 8 | 7 | 8 | 7 | 2 | 4 | 4 | 8 | 8 | 3 | 6 |
| Nutsedge | 1 | 5 | 1 | 0 | 1 | 0 | 0 | 0 | — | 1 | — | 0 | 1 | — | — | 2 | 2 | 7 | — | 0 |
| Rape | 0 | 4 | 4 | 8 | 0 | 6 | 3 | 2 | 5 | 5 | 0 | 4 | 9 | 8 | 9 | 8 | 5 | 7 | 6 | 8 |
| Rice | 1 | 0 | 1 | 1 | 1 | 0 | 0 | 1 | 1 | 1 | 0 | 1 | 2 | 1 | 2 | 1 | 2 | 3 | 1 | 2 |
| Sorghum | 3 | 0 | 2 | 1 | 0 | 0 | 0 | 1 | 1 | 1 | 1 | 1 | 2 | 1 | 2 | 2 | 2 | 3 | 2 | 1 |
| Soybean | 5 | 5 | 6 | 6 | 1 | 5 | 4 | 6 | 6 | 7 | 5 | 8 | 5 | 5 | 7 | 6 | 7 | 8 | 7 | 5 |
| Sugar beet | 6 | 9 | 8 | 8 | 2 | 8 | 8 | 5 | 8 | 7 | 8 | 9 | 9 | 9 | 9 | 9 | 9 | 9 | 9 | 9 |

TABLE A-continued

| | | | | | | | | | | | | | | | | | | |
|---|---|---|---|---|---|---|---|---|---|---|---|---|---|---|---|---|---|---|
| Velvetleaf | 1 | 0 | 3 | 2 | 1 | 3 | 0 | 1 | 3 | 6 | 2 | 2 | 7 | 3 | 4 | 5 | 7 | 8 | 1 | 1 |
| Wheat | 0 | 0 | 0 | 1 | 0 | 0 | 0 | 0 | 0 | 3 | 2 | 2 | 2 | 4 | 3 | 4 | 3 | 3 | 0 | 3 |
| Wild buckwheat | 2 | 1 | 2 | 3 | 2 | 3 | 2 | 1 | 1 | 2 | 3 | 3 | 6 | 8 | 7 | 6 | 7 | 7 | 4 | 6 |
| Wild oat | 1 | 0 | 2 | 6 | 0 | 0 | 0 | 1 | 3 | 4 | 4 | 4 | 8 | 6 | 8 | 8 | 6 | 8 | 3 | 4 |

| | COMPOUND Rate (100 g/ha) | | | | | | | | | | | | |
|---|---|---|---|---|---|---|---|---|---|---|---|---|---|
| | 2 | 6 | 7 | 8 | 9 | 10 | 11 | 12 | 13 | 14 | 15 | 16 | 17 |
| POST-EMERGENCE | | | | | | | | | | | | | |
| Barley | 0 | 1 | 0 | 0 | 0 | 2 | 1 | 2 | 2 | 2 | 2 | 0 | 0 |
| Barnyardgrass | 1 | 2 | 2 | 1 | 2 | 2 | 2 | 3 | 1 | 2 | 4 | 2 | 3 |
| Bedstraw | 2 | 7 | 4 | 3 | 3 | 6 | 4 | 5 | 4 | 3 | 3 | 2 | 3 |
| Blackgrass | 0 | 2 | 2 | 2 | 2 | 3 | 2 | 2 | 4 | 4 | 2 | 2 | 2 |
| Cheatgrass | 1 | 2 | 0 | 0 | 0 | 3 | 1 | 2 | 3 | 2 | 2 | 1 | 0 |
| Chickweed | 3 | 7 | 5 | 2 | 4 | 5 | 3 | 5 | 3 | 5 | 5 | 4 | 7 |
| Cocklebur | 2 | — | — | — | — | — | — | — | — | 5 | 2 | 2 | — |
| Corn | 1 | 1 | 1 | 1 | 1 | 2 | 1 | 2 | 2 | 1 | 3 | 1 | 2 |
| Cotton | 7 | 7 | 2 | 0 | 3 | 8 | 5 | 6 | 3 | 9 | 9 | 5 | 5 |
| Crabgrass | 1 | 2 | 1 | 2 | 4 | 4 | 2 | 3 | 2 | 3 | 7 | 2 | 3 |
| Giant foxtail | 1 | 2 | 1 | 1 | 1 | 3 | 1 | 4 | 2 | 2 | 3 | 2 | 3 |
| Lambsquarters | 3 | 5 | 4 | 2 | 4 | 5 | 3 | 5 | 5 | 9 | 10 | 6 | 10 |
| Morningglory | 3 | 3 | 6 | 2 | 5 | 5 | 3 | 2 | 2 | 6 | 2 | 3 | 5 |
| Nutsedge | 0 | 0 | 0 | 0 | 0 | 0 | 1 | 1 | 0 | 0 | 0 | 0 | 1 |
| Rape | 0 | 7 | 2 | 0 | 0 | 6 | 7 | 6 | 6 | 2 | 4 | 6 | 5 |
| Rice | 0 | 1 | 0 | 0 | 0 | 1 | 1 | 2 | 0 | 1 | 1 | 1 | 1 |
| Sorghum | 0 | 2 | 1 | 1 | 1 | 1 | 1 | 2 | 2 | 1 | 2 | 1 | 1 |
| Soybean | 4 | 5 | 4 | 3 | 7 | 4 | 4 | 4 | 6 | 3 | 7 | 5 | 6 |
| Sugar beet | 7 | 8 | 5 | 7 | 7 | 9 | 8 | 8 | 8 | 9 | 8 | 9 | 8 |
| Velvetleaf | 1 | 2 | 2 | 1 | 3 | 4 | 1 | 4 | 2 | 2 | 1 | 1 | 1 |
| Wheat | 0 | 2 | 0 | 0 | 0 | 3 | 1 | 1 | 2 | 2 | 2 | 0 | 0 |
| Wild buckwheat | 1 | 2 | 2 | 2 | 2 | 5 | 5 | 7 | 2 | 4 | 3 | 2 | 5 |
| Wild oat | 0 | 1 | 0 | 0 | 2 | 6 | 4 | 5 | 5 | 3 | 3 | 2 | 1 |

| | COMPOUND | | | | | | | | | | | | | | | | |
|---|---|---|---|---|---|---|---|---|---|---|---|---|---|---|---|---|---|
| | Rate (2000 g/ha) | | | | Rate (400 g/ha) | | | | | | | | | | | | |
| | 1 | 3 | 4 | 5 | 1 | 2 | 3 | 4 | 5 | 7 | 8 | 9 | 10 | 11 | 12 | 13 | 14 | 15 | 16 | 17 |
| PRE-EMERGENCE | | | | | | | | | | | | | | | | | | | | |
| Barley | 0 | 0 | 2 | 3 | 0 | 0 | 0 | 0 | 2 | 3 | 2 | 2 | 3 | 3 | 2 | 5 | 5 | 9 | 2 | 1 |
| Barnyardgrass | 0 | 0 | 9 | 8 | 0 | 0 | 0 | 1 | 7 | 8 | 5 | 10 | 8 | 7 | 2 | 7 | 10 | 10 | 8 | 9 |
| Bedstraw | 0 | 0 | 3 | 10 | 0 | 5 | 0 | 0 | 7 | 6 | 2 | 8 | 10 | 7 | 8 | 9 | 10 | 10 | 2 | 3 |
| Blackgrass | 0 | 0 | 3 | 9 | 0 | 0 | 0 | 0 | 10 | 9 | 10 | 10 | 5 | 8 | 9 | 10 | 9 | 10 | 10 | 9 |
| Cheatgrass | 0 | 0 | 4 | 9 | 0 | 0 | 0 | 2 | 9 | 4 | 8 | 10 | 5 | 8 | 7 | 10 | 9 | 10 | 4 | 6 |
| Chickweed | 0 | 2 | 10 | 10 | 0 | 7 | 0 | 10 | 10 | 3 | 3 | 7 | 9 | 9 | 10 | 10 | 10 | 10 | 10 | 9 |
| Cocklebur | 0 | — | — | — | — | 0 | — | — | — | — | — | — | 2 | 4 | 1 | 2 | 5 | 5 | 2 | 0 |
| Corn | 1 | 0 | 1 | 2 | 0 | 0 | 0 | 1 | 3 | 1 | 2 | 2 | 2 | 2 | 1 | 5 | 3 | 3 | 1 | 2 |
| Cotton | 0 | 0 | 0 | 4 | 0 | 0 | 0 | 0 | 0 | 0 | 0 | 0 | 1 | 1 | 1 | 2 | 0 | 1 | 0 | 0 |
| Crabgrass | 1 | 2 | 10 | 10 | 0 | 5 | 2 | 8 | 10 | 10 | 9 | 10 | 9 | 9 | 10 | 10 | 10 | 10 | 9 | 10 |
| Giant foxtail | 1 | 5 | 10 | 10 | 0 | 6 | 2 | 7 | 10 | 10 | 10 | 10 | 10 | 9 | 10 | 10 | 10 | 10 | 10 | 10 |
| Lambsquarters | 0 | 10 | 10 | 10 | 0 | 7 | 8 | 10 | 10 | 9 | 10 | 10 | — | 10 | — | 10 | 10 | 10 | 10 | 10 |
| Morningglory | 0 | 0 | 3 | 8 | 0 | 0 | 0 | 0 | 5 | 1 | 1 | 5 | 5 | 5 | 2 | 5 | 5 | 6 | 1 | 2 |
| Nutsedge | 6 | 0 | — | 2 | 0 | 0 | 0 | — | 0 | 0 | 0 | 3 | — | 0 | 0 | 0 | — | — | — | 5 |
| Rape | 0 | 0 | 2 | 6 | 0 | 1 | 0 | 0 | 7 | 3 | 2 | 2 | 10 | 7 | 4 | 10 | 6 | 10 | 2 | 2 |
| Rice | 2 | 1 | 2 | 2 | 1 | 0 | 0 | 1 | 1 | 1 | 0 | 2 | 1 | 1 | 1 | 1 | 1 | 1 | 2 | 0 |
| Sorghum | 0 | 0 | 2 | 2 | 0 | 0 | 0 | 1 | 1 | 1 | 10 | 3 | 2 | 1 | 1 | 5 | 2 | 2 | 2 | 1 |
| Soybean | 0 | 0 | 2 | 1 | 0 | 0 | 0 | 0 | 0 | 0 | 0 | 1 | 2 | 1 | 2 | 2 | 1 | 2 | 1 | 0 |
| Sugar beet | 0 | 0 | 9 | 10 | 0 | 2 | 0 | 2 | 9 | 7 | 8 | 8 | 10 | 9 | 7 | 10 | 10 | 10 | 9 | 9 |
| Velvetleaf | 1 | 1 | 6 | 10 | 0 | 0 | 0 | 0 | 6 | 1 | 2 | 10 | 2 | 5 | 1 | 3 | 7 | 10 | 1 | 0 |
| Wheat | 0 | 0 | 3 | 3 | 0 | 0 | 0 | 0 | 3 | 2 | 3 | 3 | 2 | 5 | 2 | 4 | 3 | 6 | 0 | 1 |
| Wild buckwheat | 0 | 2 | 4 | 8 | 0 | 0 | 0 | 5 | 6 | 4 | 4 | 8 | 7 | 9 | 8 | 7 | 7 | 10 | 9 | 4 |
| Wild oat | 0 | 2 | 8 | 9 | 0 | 2 | 0 | 4 | 9 | 9 | 9 | 9 | 7 | 8 | 9 | 9 | 10 | 10 | 6 | 9 |

| | COMPOUND Rate (100 g/ha) | | | | | | | | | | | | |
|---|---|---|---|---|---|---|---|---|---|---|---|---|---|
| | 2 | 6 | 7 | 8 | 9 | 10 | 11 | 12 | 13 | 14 | 15 | 16 | 17 |
| PRE-EMERGENCE | | | | | | | | | | | | | |
| Barley | 0 | 2 | 0 | 0 | 2 | 2 | 2 | 1 | 1 | 2 | 4 | 0 | 0 |
| Barnyardgrass | 0 | 2 | 3 | 1 | 4 | 4 | 4 | 1 | 5 | 3 | 10 | 2 | 3 |
| Bedstraw | 2 | 6 | 2 | 0 | 3 | 4 | 2 | 3 | 3 | 3 | 10 | 1 | 2 |
| Blackgrass | 0 | 6 | 8 | 7 | 9 | 5 | 5 | 5 | 4 | 6 | 10 | 0 | 3 |
| Cheatgrass | 0 | 7 | 2 | 3 | 9 | 6 | 4 | 3 | 5 | 6 | 10 | 0 | 2 |
| Chickweed | 0 | 8 | 0 | 0 | 2 | 6 | 3 | 5 | 8 | 2 | 10 | 0 | 7 |
| Cocklebur | 0 | — | — | — | — | 0 | — | 0 | 0 | 1 | 3 | 0 | 0 |
| Corn | 0 | 1 | 1 | 0 | 1 | 1 | 1 | 1 | 1 | 1 | 1 | 1 | 1 |
| Cotton | 0 | 0 | 0 | 0 | 0 | 0 | 0 | 0 | 1 | 0 | 0 | 0 | 0 |
| Crabgrass | 1 | 7 | 9 | 8 | 9 | 9 | 7 | 9 | 9 | 9 | 10 | 9 | 10 |
| Giant foxtail | 1 | 9 | 10 | 9 | 10 | 9 | 9 | 9 | 9 | 10 | 10 | 9 | 9 |
| Lambsquarters | 0 | — | 0 | 3 | 5 | 10 | 8 | 0 | 10 | 10 | 10 | 0 | 10 |
| Morningglory | 0 | 1 | 0 | 0 | 2 | 1 | 0 | 0 | 1 | 1 | 6 | 1 | 0 |

TABLE A-continued

| | | | | | | | | | | | | | |
|---|---|---|---|---|---|---|---|---|---|---|---|---|---|
| Nutsedge | 0 | 0 | 0 | — | — | 0 | 0 | 0 | 0 | 0 | — | 0 | 0 |
| Rape | 0 | 2 | 2 | 0 | 0 | 1 | 1 | 1 | 7 | 1 | 6 | 0 | 0 |
| Rice | 0 | 0 | 0 | 0 | 0 | 0 | 0 | 0 | 0 | 0 | 1 | 0 | 0 |
| Sorghum | 0 | 1 | 1 | 0 | 0 | 1 | 1 | 0 | 1 | 0 | 1 | 0 | 1 |
| Soybean | 0 | 1 | 0 | 0 | 0 | 1 | 1 | 0 | 1 | 0 | 1 | 0 | 0 |
| Sugar beet | 0 | 4 | 4 | 4 | 7 | 8 | 7 | 5 | 6 | 9 | 9 | 8 | 7 |
| Velvetleaf | 0 | 0 | 0 | 0 | 1 | 0 | 1 | 0 | 1 | 1 | 3 | 0 | 0 |
| Wheat | 0 | 1 | 0 | 0 | 2 | 1 | 0 | 1 | 1 | 1 | 2 | 0 | 0 |
| Wild buckwheat | 0 | 7 | 0 | 2 | 2 | 5 | 7 | 0 | 2 | 5 | 9 | 2 | 0 |
| Wild oat | 0 | 4 | 3 | 4 | 9 | 5 | 4 | 4 | 8 | 8 | 8 | 2 | 3 |

What is claimed is:

1. A compound of the formula

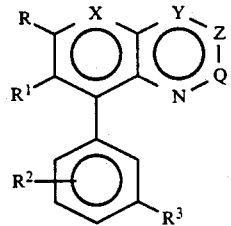

wherein
X is CH;
Y is N;
Z, $CR^4$ or $CR^5$;
Q, $CR^4$ or $CR^5$;
R is $C_1$-$C_4$ alkyl, $C_2$-$C_4$ alkoxyalkyl, $C_2$-$C_4$ alkenyl, $C_2$-$C_4$ alkynyl, $C_1$-$C_4$ alkoxy, $C_1$-$C_4$ alkylthio, $C_1$-$C_3$ alkylamino or $N(C_1$-$C_3$ alkyl)($C_1$-$C_3$ alkyl);
$R^1$ is H, F, Cl or $CH_3$;
$R^2$ is H, halogen, $C_1$-$C_3$ alkyl, $C_1$-$C_3$ haloalkyl, $C_1$-$C_3$ alkoxy or $C_1$-$C_3$ haloalkoxy;
$R^3$ is H, halogen, $C_1$-$C_4$ alkyl, $C_2$-$C_4$ alkenyl, $C_2$-$C_4$ alkynyl, $C_1$-$C_4$ haloalkyl, $C_3$-$C_4$ halocycloalkyl, $C_2$-$C_4$ haloalkenyl, $C_2$-$C_4$ haloalkynyl, $OR^6$, $S(O)_nR^7$ or CN;
$R^4$ is H, CN, $C_1$-$C_3$ alkyl, $C_1$-$C_3$ alkoxy or halogen;
$R^5$ is $C_1$-$C_4$ haloalkyl, $C_3$-$C_5$ halocycloalkyl, $C_2$-$C_4$ haloalkenyl, $C_2$-$C_4$ haloalkynyl, $OR^6$, $S(O)_nR^7$ or halogen;
$R^6$ is $C_1$-$C_4$ alkyl, $C_3$-$C_4$ alkenyl, $C_3$-$C_4$ alkynyl, $C_1$-$C_4$ haloalkyl, $C_2$-$C_4$ haloalkenyl or $C_2$-$C_4$ haloalkynyl;
$R^7$ is $C_1$-$C_2$ alkyl or $C_1$-$C_2$ haloalkyl;
$R^8$ is H, CN, $C_1$-$C_3$ alkyl, $C_1$-$C_3$ alkoxy or halogen; and
n is 0; 1 or 2;
or their mono N-oxides or their agriculturally suitable salts, provided that:
(a) when Z is $CR^4$, then Q is $CR^5$; and
(b) when Q is $CR^4$, then Z is $CR^5$.

2. The compounds of claim 1 wherein
$R^1$ is H or F; and
$R^2$ is H or F.

3. The compounds of claim 2 wherein
$R^3$ is F, Cl, Br, $C_1$-$C_4$ haloalkyl, $OR^6$, $S(O)_nR^7$ or CN;
n is 0;
Y is N; and
their mono N-oxides.

4. The compounds of claim 3 wherein
R is $C_1$-$C_3$ alkyl, $C_2$-$C_3$ alkoxyalkyl, $C_2$-$C_3$ alkenyl, $C_2$-$C_3$ alkynyl, $C_1$-$C_2$ alkoxy, $C_1$-$C_2$ alkylthio, $C_1$-$C_2$ alkylamino and $N(C_1$-$C_2$ alkyl)($C_1$-$C_2$ alkyl);
$R^6$ is $C_1$-$C_3$ alkyl, allyl, propargyl, $C_1$-$C_3$ haloalkyl, $C_2$-$C_3$ haloalkenyl.

5. The compounds of claim 4 wherein Z is CH or C—CN.

6. The compound of claim 1 which is:
2-(difluoromethoxy)-6-methyl-8-[3-(trifluoromethyl)-phenyl]quinoxaline.

7. The compound of claim 1 which is:
6-methyl-2-(trifluoromethyl)-8-[3-(trifluoromethyl)-phenyl]quinoxaline.

8. A composition suitable for controlling the growth of undesired vegetation which comprises an effective amount of a compound of claim 1 and at least one of the following: surfactant, solid or liquid diluent.

9. A composition suitable for controlling the growth of undesired vegetation which comprises an effective amount of a compound of claim 2 and at least one of the following: surfactant, solid or liquid diluent.

10. A composition suitable for controlling the growth of undesired vegetation which comprises an effective amount of a compound of claim 3 and at least one of the following: surfactant, solid or liquid diluent.

11. A composition suitable for controlling the growth of undesired vegetation which comprises an effective amount of a compound of claim 4 and at least one of the following: surfactant, solid or liquid diluent.

12. A composition suitable for controlling the growth of undesired vegetation which comprises an effective amount of a compound of claim 5 and at least one of the following: surfactant, solid or liquid diluent.

13. A composition suitable for controlling the growth of undesired vegetation which comprises an effective amount of a compound of claim 6 and at least one of the following: surfactant, solid or liquid diluent.

14. A composition suitable for controlling the growth of undesired vegetation which comprises an effective amount of a compound of claim 7 and at least one of the following: surfactant, solid or liquid diluent.

15. A method for controlling the growth of undesired vegetation which comprises applying to the locus to be protected an effective amount of a compound of claim 1.

16. A method for controlling the growth of undesired vegetation which comprises applying to the locus to be protected an effective amount of a compound of claim 2.

17. A method for controlling the growth of undesired vegetation which comprises applying to the locus to be protected an effective amount of a compound of claim 3.

18. A method for controlling the growth of undesired vegetation which comprises applying to the locus to be protected an effective amount of a compound of claim 4.

19. A method for controlling the growth of undesired vegetation which comprises applying to the locus to be protected an effective amount of a compound, of claim 5.

20. A method for controlling the growth of undesired vegetation which comprises applying to the locus to be protected an effective amount of a compound of claim 6.

21. A method for controlling the growth of undesired vegetation which comprises applying to the locus to be protected an effective amount of a compound of claim 7.

* * * * *

UNITED STATES PATENT AND TRADEMARK OFFICE
CERTIFICATE OF CORRECTION

PATENT NO. : 5,110,347
DATED : May 5, 1992
INVENTOR(S) : Thomas Selby

It is certified that error appears in the above-identified patent and that said Letters Patent is hereby corrected as shown below:

Column 45 line 30, "Z, $CR^4$ or $CR^5$;" should read --Z is $CR^4$ or $CR^5$;--.

Column 45 line 31, "Q, $CR^4$ or $CR^5$;" should read --Q is $CR^4$ or $CR^5$;--.

Signed and Sealed this

Third Day of August, 1993

Attest:

Attesting Officer

MICHAEL K. KIRK

Acting Commissioner of Patents and Trademarks